United States Patent [19]

Kukolja et al.

[11] B 4,005,074

[45] Jan. 25, 1977

[54] PROCESS FOR CLEAVING AN IMIDO SIDE CHAIN FROM PENICILLINS AND CEPHALOSPORINS

[75] Inventors: Stjepan P. Kukolja, Indianapolis; Steven R. Lammert, Greenwood, both of Ind.

[73] Assignee: Eli Lilly and Company, Indianapolis, Ind.

[22] Filed: June 18, 1973

[21] Appl. No.: 371,095

[44] Published under the second Trial Voluntary Protest Program on March 23, 1976 as document No. B 371,095.

[52] U.S. Cl. .................... 260/239.1; 260/243 C; 424/271; 424/246

[51] Int. Cl.$^2$ ................................ C07D 501/20

[58] Field of Search .................. 260/243 C

[56] References Cited

UNITED STATES PATENTS

| 3,487,074 | 12/1969 | Shechan | 260/239.1 |
| 3,843,682 | 10/1974 | Kukolja et al. | 260/243 C |

*Primary Examiner*—Nicholas S. Rizzo
*Attorney, Agent, or Firm*—William C. Martens, Jr.; Everet F. Smith

[57] ABSTRACT

The amic acid group of a 7-(amic acid) cephalosporin or 6-(amic acid) penicillin is cleaved by dehydration to the corresponding novel 7-isoimidocephalosporin or 6-isoimidopenicillin, and cleavage of the 7-isoimidocephalosporin or 6-isoimidopenicillin to the corresponding 7-aminocephalosporin or 6-aminopenicillin or to a corresponding 7-acylamidocephalosprin or 6-acylamidopenicillin.

59 Claims, No Drawings

PROCESS FOR CLEAVING AN IMIDO SIDE CHAIN FROM PENICILLINS AND CEPHALOSPORINS

BACKGROUND OF THE INVENTION

This invention relates to a process for selectively cleaving an amic acid function from a cephalosporin having an amic acid function in its 7-position, or from a penicillin having an amic acid function in its 6-position and to compounds useful as intermediates in this process.

It has been a customary practice for some time in the development of cephalosporin or penicillin antibiotics to employ an imide substituent in the 7- or 6-position when that portion of the molecule was not the point of investigation. The presence of such a protective group, particularly the phthalimido group, tended to render this position chemically quite inert and afforded the possibility to modify other portions of the molecule rather extensively with the relative assurance that this position would remain intact.

However, it has long been recognized that the presence of an imide function in the 7-position of a cephalosporin or the 6-position of a penicillin rendered the structure antibiotically only minimally active. Unfortunately, it has been impossible successfully to cleave an imido group from a cephalosporin or penicillin to liberate the protected amino group. Thus, the investigator was left with a stable substituent in this position which afforded a penicillin or cephalosporin exhibiting only minimal antibiotic activity. The use of such a substituent thus could be attractive commercially only if it could conveniently be removed at any desired point in a synthetic scheme.

It is not intended by the above to say, in general, that it has been impossible successfully to cleave an imide group. Several methods for accomplishing this are recognized. The Japanese publication by Minoru Shindo, "Cleavage Reactions of the Phthalimido Group", Yuki Gosei Kagaku Kyokai Shi, 29 (5), (1971) pp. 496–509, contains an extensive discussion of cleavage techniques. Any of these would be available in achieving cleavage of the imide function from a cephalosporin or penicillin were this the only essential consideration. However, it is at least of equal importance to employ conditions which will accomplish cleavage without sacrificing the structual integrity of the cephalosporin or penicillin molecule. To date, this has been impossible to achieve.

It has been possible to achieve a partial cleavage of the imide side chain of a cephalosporin- or penicillin-like structure to form the corresponding amic acid side chain (see, for example, Sheehan et al., Journal of the American Chemical Society, 73, (1951) pp. 4367–4372; Sheehan et al., Journal of the American Chemical Society, 78, (1956) pp. 3680–3683; Perron et al., Journal of Organic Chemistry, 7, (1964) pp. 483–487). The phthalimide function has been converted to the corresponding phthalamic acid by alkaline hydrolysis such as is described in the first Sheehan publication. However, as noted in the second Sheehan publication, all attempts to carry the cleavage beyond this point have met with failure, the β-lactam ring of the penicillin being preferentially opened with destruction of the penicillin.

Sheehan, U.S. Pat. No. 3,487,074, discloses the cleavage of 6-phthalimido-3-penamyl-carboxylic acid by treatment thereof with hydrazine hydrate in dioxane for 12 hours at room temperature. However, this method has been found to be unsuccessful when applied to penicillins and cephalosporins, although moderate success was experienced when this approach was applied to a 7-phthalimido Δ²-cephalosporin [see Spry, D. O., Journal of the American Chemical Society, 92, (1970), p. 5007].

A method has now been discovered by which an amic acid function of a cephalosporin or penicillin can be cleaved without opening the β-lactam ring. This invention comprises such a method. Normally, the amic acid function will be obtained from partial cleavage of an imide function; however, this is by no means essential. Another aspect of this invention is directed to novel intermediates useful in achieving cleavage of the amic acid function as well as to separate conversion steps in the overall cleavage process.

SUMMARY OF THE INVENTION

Thus, this invention is directed to a process for cleaving the amic acid function of a compound having the formula

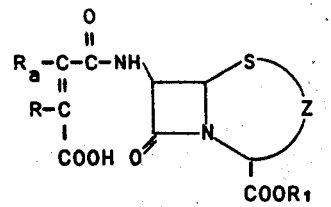

in which R and $R_a$ are hydrogen, or R and $R_a$ taken together with the carbon atoms to which they are attached represent an ortho-phenylene ring,
Z is

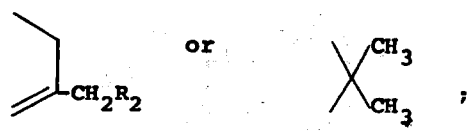

$R_1$ is hydrogen or a carboxy protecting group; and $R_2$ is hydrogen, acetoxy, methoxy, methylthio, (5-methyl-1,3,4-thiadiazol-2-yl)thio, or (1-methyl-1H-tetrazol-5-yl)thio; which comprises 1. dehydrating said compound to form the corresponding isoimide having the formula

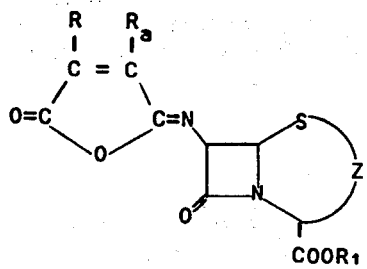

2. reacting said isoimide with a hydrazine of the formula

in which $R_3$ and $R_4$ independently are hydrogen or methyl; and 3. a. reacting the reaction mixture from the aforementioned hydrazine treatment with an acyl halide to produce the corresponding 7-acylamido cephalosporin or 6-acylamido penicillin; or b. when at least one of $R_3$ and $R_4$ is methyl, recovering the corresponding 7-amino cephalosporin or 6-amino penicillin from the reaction mixture of the aforementioned hydrazine treatment; or c. when $R_3$ and $R_4$ are hydrogen, heating the reaction mixture from the aforementioned hydrazine treatment to a temperature of from about 50°C. to about 100°C. to produce the corresponding 7-amino cephalosporin or 6-amino penicillin; or d. when $R_3$ and $R_4$ are hydrogen, reacting the reaction mixture from the aforementioned hydrazine treatment with acid to produce the corresponding 7-amino cephalosporin or 6-amino penicillin in the form of its acid addition salt.

Another aspect of this invention is a process for preparing an isoimide of the formula

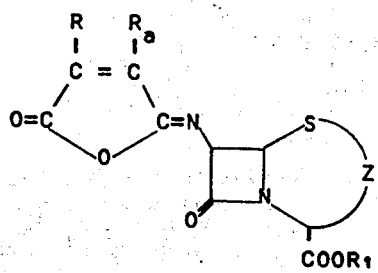

which comprises dehydrating an amic acid of the formula

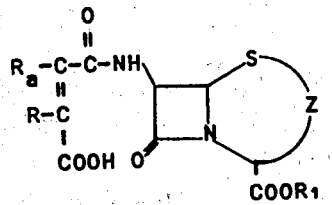

in which, in the above formulae,

R, $R_a$, Z, and $R_1$ have the previously designated meanings.

A further aspect of this invention is a process for cleaving the isoimido function of an isoimide compound having the formula

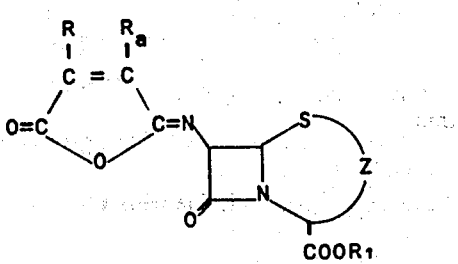

in which R, $R_a$, Z, and $R_1$ have the previously designated meanings; which comprises (1) reacting said isoimide compound with a hydrazine of the formula $R_3HNNHR_4$ in which $R_3$ and $R_4$ independently are hydrogen or methyl; and, 2. a. reacting the reaction mixture from the aforementioned hydrazine treatment with an acyl halide to produce the corresponding 7-acylamido cephalosporin or 6-acylamido penicillin; or b. when at least one of $R_3$ and $R_4$ is methyl, recovering the corresponding 7-amino cephalosporin or 6-amino penicillin from the reaction mixture of the aforementioned hydrazine treatment; or c. when $R_3$ and $R_4$ are hydrogen, heating the reaction mixture from the aforementioned hydrazine treatment to a temperature of from about 50°C. to about 100°C. to produce the corresponding 7-amino cephalosporin or 6-amino penicillin; or d. when $R_3$ and $R_4$ are hydrogen, reacting the reaction mixture from the aforementioned hydrazine treatment with acid to produce the corresponding 7-amino cephalosporin or 6-amino penicillin in the form of its acid addition salt.

A further aspect of this invention are compounds useful as intermediates in the process of this invention and having the formula

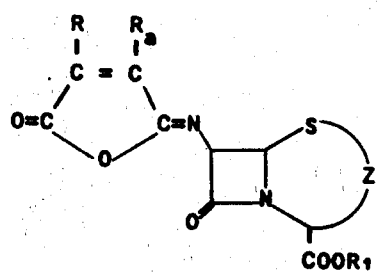

in which R, $R_a$, Z, and $R_1$ have the previously designated meanings.

DETAILED DESCRIPTION OF THE INVENTION

Unless otherwise specifically mentioned, as used herein, the terms "cleavage", "cleaving", and the like, are intended to refer to the removal of a substituent in the 7-position of a cephalosporin or the 6-position of a penicillin thereby to produce a free 7-amino cephalosporin or 6-amino penicillin, any of such compounds in the form of their acid addition salts, or any of such compounds resulting from the removal of the 7- or 6-substituent and which have been re-acylated to contain another acyl substituent in their respective 7- or 6-positions.

In accordance with one aspect of the process of this invention, a first step involves dehydration of the amic acid function to produce the corresponding isoimide. When, in the amic acid structure, R and $R_a$ taken together with the carbon atoms to which they are attached represent an ortho phenylene ring, the source of the amic acid generally will be a phthalimido compound which has been partially cleaved by recognized techniques. The structure of the resulting phthalamic acid is as follows:

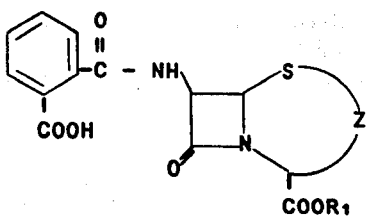

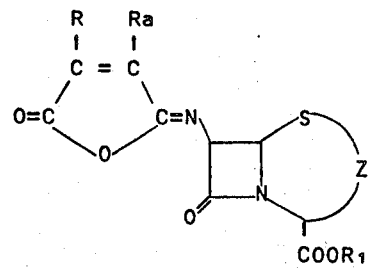

The preparation of a compound having the above structure from the corresponding phthalimido compound is well recognized in the art, and any of the conditions therein defined can be employed. A typical method by which partial cleavage is effected involves an alkaline hydrolysis such as is described in Sheehan et al., Journal of the American Chemical Society, 73, (1951), pp. 4367–4372.

The conditions of alkaline hydrolysis which can be employed to accomplish partial cleavage to the amic acid include use of an alkali metal hydroxide or sulfide, such as sodium hydroxide, potassium hydroxide, lithium hydroxide, sodium sulfide, potassium sulfide, lithium sulfide, and the like. Generally, from about 1 to about 2 equivalents of the alkali metal hydroxide or sulfide are employed, except in the instance in which the free acid of the cephalosporin or penicillin is employed, in which case the free carboxyl itself will consume one equivalent of the alkaline reagent and therefore an additional equivalent will be required.

In general, the pH of the reaction medium ranges from about 9 to about 11. This is achieved generally by use of an aqueous medium containing an inert, water-miscible organic solvent, such as, for example, tetrahydrofuran, N,N-dimethylformamide, acetone, dimethylsulfoxide, dioxane, and the like.

The partial cleavage generally is quite rapid, typically being completed in from about 3 to about 30 minutes, and more typically in from about 5 to about 10 minutes. The temperature of reaction usually is from about −10°C. to about room temperature, and preferably, about 0°C.

The amic acid can also have the formula

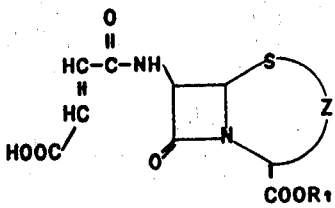

The above amic acid, as well as the phthalamic acid defined herein, are also available from sources other than their corresponding imide precursors. For example, the free amino compound can be reacted with the appropriate anhydride, for example, maleic anhydride, to produce the corresponding amic acid compound, specifically, in this case, the 3-carboxyacrylamido compound.

The dehydration step of the process of this invention comprises the conversion of the amic acid to an isoimide. The isoimides which are thereby produced are new compounds and are a part of this invention. They have the formula Several methods are available for converting the amic acid to the isoimide. One of these involves the use of a dehydrating agent, such as N,N'-dicyclohexylcarbodiimide (DCC), N-ethoxycarbonyl-2-ethoxy-1,3-dihydroquinoline (EEDQ), 1-cyclohexyl-3-(2-morpholinoethyl)carbodiimide metho-p-toluenesulfonate, 1-ethyl-3-(3-dimethylaminopropyl)carbodiimide hydrochloride, N-trifluoroacetylimidazole, and the like. Preferably, for reasons of convenience, DCC is employed. Typically, a 1:1 equivalent of the DCC and the amic acid are mixed in a suitable solvent. It is possible to employ an excess of the DCC; however, it is highly preferred to employ an equivalent amount based upon the amount of the amic acid since, in general, any excess DCC is difficult to remove from the product. It, of course, is possible to use a lesser quantity of the DCC relative to the amic acid; however, this will result in the undesirable incomplete conversion of the amic acid. Generally, therefore, equivalent amounts of the amic acid and DCC are mixed together in a suitable solvent, specifically an aprotic solvent, that is, one which does not offer or accept protons. A wide variety of such solvents are known to those skilled in the art and can be used in accordance with the process of this invention. Included as such solvents are N,N-dimethylformamide, N,N-dimethylacetamide, tetrahydrofuran, dioxane, aliphatic nitriles, such as acetonitrile, propionitrile, and the like; aromatic hydrocarbons and halogenated derivatives, such as benzene, toluene, dichlorobenzene, and the like; and aliphatic halogenated hydrocarbons, such as methylene chloride, chloroform, bromoform, carbon tetrachloride, carbon tetrabromide, ethylene dichloride, ethylene dibromide, and the like.

The DCC and the amic acid are allowed to react in the inert medium at a temperature of from about 0°C. to about 30°C. for from about 15 minutes to about 2 hours, and preferably for about 1 hour. The isoimide thereby formed is recovered from the reaction mixture in accordance with standard techniques.

Another method which is available in converting the amic acid to an isoimide involves the reaction of the amic acid with trifluoroacetic anhydride in the presence of a tertiary amine.

The reaction typically is carried out in an aprotic solvent such as any of those mentioned hereinabove. A tertiary amine, such as N-methylmorpholine, triethylamine, pyridine, quinoline, N,N-dimethylaniline, etc., in an amount of from about 1 to about 2 moles per mole of the amic acid is mixed with the amic acid in the aprotic solvent, and a molar equivalent or a slight excess of trifluoroacetic anhydride relative to the amic acid is added. A moderate excess of trifluoroacetic anhydride can be employed if the reaction medium is substantially water-free. The presence in the reaction medium of a significant quantity of water will decompose the trifluoroacetic anhydride to produce trifluoroacetic acid which, due to its protic nature, is detrimental to the reaction.

The reaction is carried out at a temperature of from about 0° C. to about 30° C. and generally is completed within from about 15 minutes to about 1 hour.

Another method of converting the amic acid to the isoimide is by reacting the amic acid with an alkyl chloroformate, such as ethyl chloroformate, propyl chloroformate, t-butyl chloroformate, isobutyl chloroformate, and the like. However, the conversion to the isoimide using an alkyl chloroformate has the drawback that $R_1$ of the amic acid compound cannot be hydrogen. Thus a carboxy-protected compound must be employed. The chloroformate reaction is carried out in the presence of a tertiary amine, such as pyridine, quinoline, triethylamine, N-methylmorpholine, N,N-dimethylaniline, and the like. As with the above conversions, this reaction typically is carried out in the presence of an aprotic organic solvent, such as any of those mentioned hereinabove. No more than one equivalent of the amine based upon the amic acid is employed, and it is highly preferred to employ a slightly deficient quantity of the amine. Any excess tertiary amine will tend to convert the amic acid to an imide, typically what may have been the original starting material in the process of this invention. A slight excess of the chloroformate can be employed; however, this is not preferred, since any excess, if present in the product to be treated in the next step of the process of this invention, will react with the hydrazine employed therein.

The reaction is carried out for from about 5 to about 40 minutes, preferably from about 20 to about 30 minutes at a temperature of from about −20° C. to about +5° C., and preferably from about −20° C. to about −5° C. The isoimide is obtained by warming the reaction mixture to room temperature upon completion of reaction and isolating it in accordance with known techniques.

The aforementioned isoimide cephalosporin or penicillin can then be selectively cleaved by a step-wise treatment thereof with a hydrazine, typically unsubstituted hydrazine, methyl hydrazine, or N,N'-dimethylhydrazine, followed by product recovery and/or further treatment depending upon the product which is desired and the particular hydrazine which is employed.

The hydrazine treatment involves the reaction of the isoimide in an inert organic solvent such as any of the aprotic solvents mentioned hereinabove with one equivalent of the hydrazine. Care must be taken to avoid the presence of any excess hydrazine. Therefore, in order to ensure the avoidance of such excess, up to one equivalent of the hydrazine per equivalent of the isoimide is employed, and, typically, a slight deficiency of hydrazine is employed. The reaction is carried out at relatively cold temperatures ranging from about −76° C. to about room temperature and preferably at about ice temperature (0° C.) or below. The hydrazine typically is added to the isoimide mixture while the mixture is at the relatively cold reaction temperature. Thus, the mixture of the isoimide in the organic solvent is maintained at the temperature of reaction while the hydrazine, previously cooled, is added. The reaction is rather rapid, generally being completed within from about 1 to 10 minutes, and the reaction generally is permitted to proceed for about an additional 5 minutes.

The particular treatment which the hydrazine reaction mixture then receives depends upon the structure of the hydrazine which is employed and the ultimate product which is desired.

The hydrazines which are used have the structure $R_3HNNHR_4$ in which $R_3$ and $R_4$ independently are hydrogen and methyl. When either or both of $R_3$ and $R_4$ are methyl, no further treatment is necessary since the free 7-amino cephalosporin or 6-amino penicillin is generated and can be isolated simply by applying techniques well recognized in the art.

When $R_3$ and $R_4$ in the hydrazine which is employed are both hydrogen, a complex of the free 7-amino cephalosporin or 6-amino penicillin and the by-product, diketophthalazine, forms, and this complex must be broken. This can be accomplished by heating the mixture or by treating the mixture with acid or, more readily, by a combination of both heat and acid treatment.

When heat is employed, the complex typically can be broken by subjecting the reaction mixture to a temperature of from about 50° C. to about 100° C. for from about 5 to about 20 minutes, and the free amino compound recovered by recognized techniques.

The diketophthalazine complex can also be broken by treating the reaction mixture with an acid. Virtually any acid, organic or inorganic, can be used. Typical such acids include, for example, hydrochloric acid, hydrobromic acid, phosphoric acid, p-toluenesulfonic acid, sulfuric acid, methanesulfonic acid, and the like. An equivalent or a moderate excess of the acid, typically up to about two equivalents of the acid, based upon the isoimide, is employed. Preferably, acid is employed in conjunction with heat, and, therefore, the resulting reaction mixture is heated to a temperature of from about 50° C. to about 100° C., and the decomposition of the complex is permitted to proceed. Depending upon the relative temperature which is employed, the reaction typically will be completed within from about 5 to about 10 minutes. When an acid is employed, the free amino cephalosporin or penicillin in the form of its acid addition salt is thereby produced and is recovered in accordance with known techniques.

It is also possible to form a 7-acylamido cephalosporin or a 6-acylamido penicillin by subjecting the hydrazine reaction mixture to treatment with an acyl halide which contains an acyl function which, in combination with the 7-amino cephalosproin or 6-amino penicillin, will form the desired acylamido function. The use of an acyl halide obviates any necessity for heat or acid treatment to decompose the diketopphthalazine complex, should such have formed, since the acyl halide itself is sufficiently acidic to accomplish the necessary decomposition. Any of the typical acyl functions can be thereby introduced into the 7-position of the cephalosporin or 6-position of the penicillin molecule simply by selection of the appropriate acyl halide, preferably the corresponding acyl chloride. The resulting acylamido cephalosporin or penicillin can be readily recovered by techniques well recognized in the art.

Typical acyl halides, each of which can be employed to produce the ultimate acylmido product are those of the formula $R_x-Y$ in which Y is a halogen, such as chlorine, bromine, or iodine, and $R_x$ is $C_1$ to $C_8$-alkanoyl;
$C_2$ to $C_8$-chloro- or bromalkanoyl;

azidoacetyl;
cyanoacetyl;
2-sydnone-3-$C_1$ to $C_3$-alkanoyl;

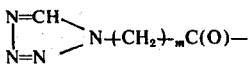

in which m is zero, 1, or 2;

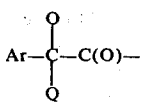

in which each Q is hydrogen or methyl, and Ar is 2-thienyl, 3-thienyl, 2-furyl, 3-furyl, 2-pyrrolyl, 3-pyrrolyl, phenyl, or phenyl substituted with chlorine, bromine, iodine, fluorine, trifluoromethyl, hydroxy, $C_1$ to $C_3$-alkyl, $C_1$ to $C_3$-alkyloxy, cyano, or nitro;

Ar—X—$CH_2$—C(O)— in which X is oxygen or sulfur, and Ar is as defined above; or Ar is 4-pyridyl in which X is sulfur; or

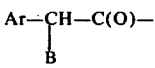

in which Ar is as defined above, and B is —$NH_2$; an amino group protected with benzyloxycarbonyl, $C_1$ to $C_4$-alkoxycarbonyl, cyclopentyloxycarbonyl, cyclohexyloxycarbonyl, benzhydryloxycarbonyl, triphenylmethyl, 2,2,2-trichloroethoxycarbonyl,

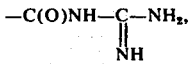

or the enamine from methyl acetoacetate or acetylacetone; —OH, or —OH protected by esterification with a $C_1$ to $C_6$-alkanoic acid; —COOH, or —COOH protected by esterification with a $C_1$ to $C_6$-alkanol; —$N_3$; —CN; or —C(O)$NH_2$.

The cephalosporin or penicillin used as starting material in the process of this invention has the following formula:

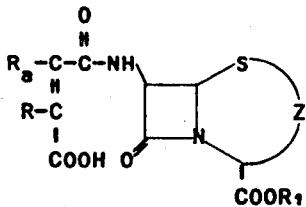

$R_1$ in the above formula as well as in the various products of the process of this invention denotes hydrogoen or a carboxy protecting group. The nature of the carboxy protecting group is not important, and any of those recognized in the art can be used. Preferably, however, this group is the residue of an ester function which is removable by acid treatment or by hydrogenation. Preferred carboxy protecting groups include, for example, $C_1$–$C_4$ alkyl, 2,2,2-trihaloethyl, benzyl, p-nitrobenzyl, p-methoxybenzyl, benzhydryl, $C_2$ to $C_6$-alkanoyloxymethyl, phenacyl, or p-halophenacyl, in any of the above of which halo denotes chlorine, bromine, or iodine. Specific illustrations of the preferred ester residues of the carboxyl group of the imido cephalosporin or penicillin compound used in the process of this invention include, for example, methyl, ethyl, n-propyl, isopropyl, n-butyl, secbutyl, isobutyl, t-butyl, 2,2,2-trichloroethyl, 2,2,2-tribromoethyl, p-nitrobenzyl, benzyl, p-methoxybenzyl, benzhydryl, acetoxymethyl, pivaloyloxymethyl, propionoxymethyl, phenacyl, p-chlorophenacyl, p-bromophenacyl, and the like.

Highly preferred ester residues are t-butyl, benzyl, p-nitrobenzyl, p-methoxybenzyl, benzhydryl, and 2,2,2-trichloroethyl.

As mentioned, $R_1$ in the above formula, in addition to being a carboxy protecting group, can also be hydrogen. Thus, the free acid cephalosporin or penicillin can be employed in the process of this invention.

Most preferably, $R_1$ is hydrogen or p-nitrobenzyl,

In the above formula, the 7-position of the cephalosporin or the 6-position of the penicillin contains a 2-carboxybenzamido group (typically derived from a phthalimido group) or a maleamido group.

Thus, the process of this invention proceeds stepwise from a (2-carboxybenzamido)- to a phthalisoimido- to an amino- or acylamido- cephalosporin or penicillin.

It is also possible to begin the process of this invention with a maleamido cephalosporin or penicillin. This step-wise sequence includes conversion of maleamido- to maleisoimido- to amino- or acylamido- cephalosporin or penicillin.

The 3-position of the 7-(amic acid) cephalosporin starting material can contain any of the following: methyl, acetoxymethyl, methoxymethyl, methtylthiomethyl, (5-methyl-1,3,4-thiadiazol-2-yl)thiomethyl, or (1-methyl-1H-tetrazol-5-yl)thiomethyl. The substituent which is present in the 3-position of the cephalosporin starting material will remain intact throughout the sequence of the process of this invention.

The following are representative of the product conversions which are available in accordance with the process of this invention. It will be understood, however, that the ratio of products may vary depending upon the particular reactants which are employed, the relative quantities of reactants, and the conditions of reaction.

Methyl 7-(2-carboxybenzamido)-3-methyl-3-cephem-4-carboxylate to methyl 7-phthalisoimido-3-methyl-3-cephem-4-carboxylate to methyl 7-amino-3-methyl-3-cephem-4-carboxylate.

2,2,2-Trichloroethyl 7-(2-carboxybenzamido)-3-acetoxymethyl-3-cephem-4-carboxylate to 2,2,2-trichloroethyl 7-phthalisoimido-3-acetoxymethyl-3-cephem-4-carboxylate to 2,2,2-trichloroethyl 7-amino-3-acetoxymethyl-3-cephem-4-carboxylate.

p-Nitrobenzyl 7-(2-carboxybenzamido)-3-methoxymethyl-3-cephem-4-carboxylate to p-nitrobenzyl 7-phthalisoimido-3-methoxymethyl-3-cephem-4-carboxylate to p-nitrobenzyl 7-amino-3-methoxymethyl-3-cephem-4-carboxylate.

Benzyl 7-(2-carboxybenzamido)-3-methylthiomethyl-3-cephem-4-carboxylate to benzyl 7-phthalisoimido-3-methylthiomethyl-3-cephem-4-carboxylate to benzyl 7-amino-3-methylthiomethyl-3-cephem-4-carboxylate.

Benzhydryl 7-(2-carboxybenzamido)-3-(5-methyl-1,3,4-thiadiazol-2-yl)-thiomethyl-3-cephem-4-carboxylate to benzhydryl 7-phthalisoimido-3-(5-methyl-1,3,4-thiadiazol-2-yl)-thiomethyl-3-cephem-4-carboxylate to benzhydryl 7-amino-3-(5-methyl-1,3,4-thiadiazol-2-yl)thiomethyl-3-cephem-4-carboxylate.

t-Butyl 7-(2-carboxybenzamido)-3-(1-methyl-1H-tetrazol-5-yl)thiomethyl-3-cephem-4-carboxylate to t-butyl 7-phthalisoimido-3-(1-methyl-1H-tetrazol-5-yl)thiomethyl-3-cephem-4-carboxylate to t-butyl 7-amino-3-(1-methyl-1H-tetrazol-5-yl)-thiomethyl-3-cephem-4-carboxylate.

p-Nitrobenzyl 7-(2-carboxybenzamido)-3-acetoxymethyl-3-cephem-4-carboxylate to p-nitrobenzyl 7-phthalisoimido-3-acetoxymethyl-3-cephem-4-carboxylate to p-nitrobenzyl 7-amino-3-acetoxymethyl-3-cephem-4-carboxylate.

p-Nitrobenzyl 7-(2-carboxybenzamido)-3-methyl-3-cephem-4-carboxylate to p-nitrobenzyl 7-phthalisoimido-3-methyl-3-cephem-4-carboxylate to p-nitrobenzyl 7-amino-3-methyl-3-cephem-4-carboxylate.

p-Nitrobenzyl 7-(2-carboxybenzamido)-3-methylthiomethyl-3-cephem-4-carboxylate to p-nitrobenzyl 7-phthalisoimido-3-methylthiomethyl-3-cephem-4-carboxylate to p-nitrobenzyl 7-amino-3-methylthiomethyl-3-cephem-4-carboxylate.

p-Nitrobenzyl 7-(2-carboxybenzamido)-3-(5-methyl-1,3,4-thiadiazol-2-yl)thiomethyl-3-cephem-4-carboxylate to p-nitrobenzyl 7-phthalisoimido-3-(5-methyl-1,3,4-thiadiazol-2-yl)thiomethyl-3-cephem-4-carboxylate to p-nitrobenzyl 7-amino-3-(5-methyl-1,3,4-thiadiazol-2-yl)thiomethyl-3-cephem-4-carboxylate.

p-Nitrobenzyl 7-(2-carboxybenzamido)-3-(1-methyl-1H-tetrazol-5-yl)thiomethyl-3-cephem-4-carboxylate to p-nitrobenzyl 7-phthalisoimido-3-(1-methyl-1H-tetrazol-5-yl)thiomethyl-3-cephem-4-carboxylate to p-nitrobenzyl 7-amino-3-(1-methyl-1H-tetrazol-5-yl(thiomethyl-3-cephem-4-carboxylate.

p-Methoxybenzyl 7-(2-carboxybenzamido)-3-acetoxymethyl-3-cephem-4-carboxylate to p-methoxybenzyl 7-phthalisoimido-3-acetoxymethyl-3-cephem-4-carboxylate to p-methoxybenzyl 7-amino-3-acetoxymethyl-3-cephem-4-carboxylate.

p-Nitrobenzyl 7-maleamido-3-methyl-3-cephem-4-carboxylate to p-nitrobenzyl 7-maleisoimido-3-methyl-3-cephem-4-carboxylate to p-nitrobenzyl 7-amino-3-methyl-3-cephem-4-carboxylate.

2,2,2-Trichloroethyl 7-maleamido-3-(1-methyl-1H-tetrazol-5-yl)thiomethyl-3-cephem-4-carboxylate to 2,2,2-trichloroethyl 7-maleisoimido-3-(1-methyl-1H-tetrazol-5-yl)thiomethyl-3-cephem-4-carboxylate to 2,2,2-trichloroethyl 7-amino-3-(1-methyl-1H-tetrazol-5-yl)thiomethyl-3-cephem-4-carboxylate.

Benzyl 7-maleamido-3-(5-methyl-1,3,4-thiadiazol-2-yl)thiomethyl-3-cephem-4-carboxylate to benzyl 7-maleisoimido-3-(5-methyl-1,3,4-thiadiazol-2-yl)thiomethyl-3-cephem-4-carboxylate to benzyl 7-amino-3-(5-methyl-1,3,4-thiadiazol-2-yl)thiomethyl-3-cephem-4-carboxylate.

Pivaloyloxymethyl 7-(2-carboxybenzamido)-3-methylthiomethyl-3-cephem-4-carboxylate to pivaloyloxymethyl 7-phthalisoimido-3-methylthiomethyl-3-cephem-4-carboxylate to pivaloyloxymethyl 7-amino-3-methylthiomethyl-3-cephem-4-carboxylate.

Acetoxymethyl 7-(2-carboxybenzamido)-3-methoxymethyl-3-cephem-4-carboxylate to acetoxymethyl 7-phthalisoimido-3-methoxymethyl-3-cephem-4-carboxylate to acetoxymethyl 7-amino-3-methoxymethyl-3-cephem-4-carboxylate.

Phenacyl 7-(2-carboxybenzamido)-3-methyl-3-cephem-4-carboxylate to phenacyl 7-phthalisoimido-3-methyl-3-cephem-4-carboxylate to phenacyl 7-amino-3-methyl-3-cephem-4-carboxylate.

p-Chlorophenacyl 7-(2-carboxybenzamido)-3-acetoxymethyl-3-cephem-4-carboxylate to p-chlorophenacyl 7-phthalisoimido-3-acetoxymethyl-3-cephem-4-carboxylate to p-chlorophenacyl 7-amino-3-acetoxymethyl-3-cephem-4-carboxylate.

7-(2-Carboxybenzamido)-3-methyl-3-cephem-4-carboxylic acid to 7-phthalisoimido-3-methyl-3-cephem-4-carboxylic acid to 7-amino-3-methyl-3-cephem-4-carboxylic acid. 7-(2-Carboxybenzamido)-3-acetoxymethyl-3-cephem-4-carboxylic acid to 7-phthalisoimido-3-acetoxymethyl-3-cephem-4-carboxylic acid to 7-amino-3-acetoxymethyl-3-cephem-4-carboxylic acid.

7-(2-Carboxybenzamido)-3-methoxymethyl-3-cephem-4-carboxylic acid to 7-phthalisoimido-3-methoxymethyl-3-cephem-4-carboxylic acid to 7-amino-3-methoxymethyl-3-cephem-4-carboxylic acid.

7-(2-Carboxybenzamido)-3-methylthiomethyl-3-cephem-4-carboxylic acid to 7-phthalisoimido-3-methylthiomethyl-3-cephem-4-carboxylic acid to 7-amino-3-methylthiomethyl-3-cephem-4-carboxylic acid.

7-(2-Carboxybenzamido)-3-(5-methyl-1,3,4-thiadiazol-2-yl)thiomethyl-3-cephem-4-carboxylic acid to 7-phthalisoimido-3-(1,3,4-methyl-1,3,4-thiadiazol-2-yl)thiomethyl-3-cephem-4-carboxylic acid to 77-amino-3-(5-methyl-1,3,4-thiadiazol-2-yl)thiomethyl-3-cephem-4-carboxylic acid.

7-(2-Carboxybenzamido)-3-(1-methyl-1H-tetrazol-5-yl)thiomethyl-3-cephem-4-carboxylic acid to 7-phthalisoimido-3-(1-methyl-1H-tetrazol-5-yl)thiomethyl-3-cephem-4-carboxylic acid to 7-amino-3-(1-methyl-1H-tetrazol-5-yl)thiomethyl-3-cephem-4-carboxylic acid.

The final product in the immediately preceding list is presented in the form of the free 7-amino compound. However, in accordance with the process of this invention, when an acid treatment is employed, it will be initially obtained in the form of its acid addition salt. This salt, of course, can be readily converted to the free 7-amino compound by well recognized techniques.

Furthermore, the process conversions illustrated hereinabove do not reflect another aspect of this invention, namely, the possibility to obtain, instead of the free 7-amino compound or the acid addition salt thereof, a corresponding 7-acylamido compound. This product is obtainable by employing an acyl halide, typically the acyl chloride, of the 7-acylamido function intended in the final product. The acyl halide is employed in place of the acid used in the final step of the cleavage process. It has been discovered that by so doing the acyl halide itself is sufficiently acidic to achieve cleavage of any intermediate which may be present in the reaction mixture from the hydrazine treatment. Concomitantly therewith, the free 7-amino group is acylated to the corresponding 7-acylamido compound.

Any of the well recognized acyl groups can be introduced into the 7-position by appropriate selection of the particular acyl halide. These include, for example, phenylacetyl, phenoxyacetyl, phenylglycyl, 2-thienylacetyl, mandelyl, and the like.

Virtually any acyl halide can be employed. Typical such acyl halides include, for example, acetyl chloride, hexanoyl bromide, chloroacetyl chloride, γ-bromooctanoyl chloride, azidoacetyl bromide, cyanoacetyl chloride, sydnoneacetyl chloride, tetrazoleacetyl chloride, 2-thienylacetyl chloride, 3-thienylacetyl bromide, 2-furylacetyl iodide, 3-furylacetyl chloride, 2-pyrrolylacetyl bromide, 3-pyrrolylacetyl chloride, phenylacetyl chloride, α,α-dimethylphenylacetyl chloride, p-chlorophenylacetyl chloride, m-bromophenylacetyl bromide, p-iodophenylacetyl chloride, p-fluorophenylacetyl chloride, m-trifluoromethylphenylacetyl bromide, p-hydroxyphenylacetyl chloride, p-tolylacetyl bromide, m-methoxyphenylacetyl chloride, p-cyanophenylacetyl chloride, p-nitrophenylacetyl bromide, phenoxyacetyl chloride, phenylthioacetyl chloride, p-hydroxyphenoxyacetyl bromide, 4-pyridylthioacetyl chloride, m-chlorophenoxyacetyl chloride, α-aminophenylacetyl chloride, N-(benzyloxycarbonyl)-α-aminophenylacetyl bromide, N-(methoxycarbonyl)-α-aminophenylacetyl chloride, N-(cyclopentyloxycarbonyl)-α-aminophenylacetyl chloride, N-(cyclohexyloxycarbonyl)-α-aminophenylacetyl chloride, N-(benzhydryloxycarrbonyl)-α-aminophenylacetyl bromide, N-(triphenylmethyl)-α-aminophenylacetyl chloride, N-(2,2,2-trichloroethoxycarbonyl)-α-aminophenylacetyl chloride, α-hydroxyphenylacetyl chloride, α-formyloxyphenylacetyl chloride, α-acetoxyphenylacetyl chloride, α-carboxyphenylacetyl chloride, α-methoxycarbonylphenylacetyl chloride, α-(t-butoxycarbonyl)phenylacetyl chloride, α-azidophenylacetyl chloride, α-cyanophenylacetyl chloride, α-carbamoylphenylacetyl chloride, and the like.

Moreover, it will be understood that any of the above-illustrated conversion sequences are also applicable to the corresponding 6-substituted penicillin compounds. It is not intended by this statement to restrict the penicillin conversions to those specifically illustrated above with respect to cephalosporins; any of those penicillins broadly defined herein can be employed. Of course, in the penicillin series, the group designated herein as $R_2$ does not exist, and therefore, in the list of representative cephalosporin conversion sequences provided hereinabove, appropriate modification is required.

The products and intermediates produced in accordance with the process of this invention can be isolated by employing conventional methods. These can include, for example, chromatographic separation, filtration, recrystallization, and the like.

When the ultimate product of the process of this invention is an ester, the product can be converted to an active antibiotic by, in addition to appropriate acylation of the free amino function, cleavage of the ester function by known techniques. Deesterification can be achieved by treatment of the ester with an acid such as trifluoroacetic acid, hydrochloric acid, and the like, or with zinc and acid, such as formic acid, acetic acid, or hydrochloric acid. It can likewise be accomplished by hydrogenating the ester in the presence of palladium, rhodium, or a compound thereof, in suspension or on a carrier such as barium sulfate, carbon, alumina, or the like.

The following examples are provided to further illustrate this invention. It is not intended that this invention be limited in scope by reason of any of these examples.

Preparation A.
7-Phthalimido-3-methyl-3-cephem-4-carboxylic acid.

To a suspension of 181 g. of 7-amino-3-methyl-3-cephem-4-carboxylic acid (7-ADCA) in 1700 ml. of water, 142 g. of $NaHCO_3$ were slowly added followed by a solution of 186 g. of N-carbethoxyphthalimide in 1 liter of acetone added dropwise over a 30 minute period. After stirring for 3 hrs. the solution was cooled in an ice-water bath and acidified to pH 2.1 by addition of 600 ml. of 42.5% of $H_3PO_4$. The resulting precipitate was filtered, washed with water, and vacuum dried to give 227 g. of a mixture of the starting material and the desired phthalimido compound. The mixture was separated by extraction with warm acetone and ethyl acetate, recovering 105 g. of 7-ADCA. The yield of the phthalimido compound was 114 g. A sample (1 g.) of product was crystallized from acetone (15 ml.); colorless crystals, m.p. 223°–225°; $[\alpha]_D$ + 428.02° (MeCN); ir (nujol) 1810, 1785, 1740 and 1710 cm$^{-1}$; nmr (CDCl$_3$) δ 2.38 (s, 3, CH$_3$), 3.0 and 3.75 (ABq, 2, J=14 Hz), 5.13 (d, 1, J=4.5 Hz), 5.71 (d, 1, J=4.5 Hz), and 7.82 (m, 4, ArH).

(Anal. calcd. for $C_{16}H_{12}N_2O_5S$: C, 55.81; H, 3.51; N, 8.14; O, 23.23; S, 9.31. Found: C, 55.72; H, 3.38; N, 8.17; O, 23.51; S, 9.27%.

Preparation B. Methyl
7-phthalimido-3-methyl-3-cephem-4-carboxylate

To a solution of 17.3 g. (0.05 mol.) of 7-phthalimido-3-methyl-3-cephem-4-carboxylic acid in 50 ml. of acetone and 20 ml. of water, 5 g. (0.05 mol.) of KHCO$_3$ were slowly added. The resulting solution was evaporated to dryness, and 38 ml. of DMF and 5 ml. of methyl iodide were added to the residue. The mixture was stirred for 3 hrs. at room temperature. To this mixture were then added 100 g. of ice, and the resulting solid product was filtered. The product was crystallized from a mixture of 100 ml. of 2-propanol and 100 ml. of acetone. Yield: 7.91 of crystals, m.p. 187°–188°; ir (CHCl$_3$) 1790 and 1735 cm$^{-1}$, nmr (CDCl$_3$) δ 2.31 (s, 3, CH$_3$), 3.0 and 3.75 (ABq, 2, J=15 Hz), 3.85 (s, 3, CH$_3$), 5.15 (d, 1, J=4.4 Hz), 5.74 (d, 1, J=4.4 Hz) and 7.73 (m, 4, ArH).

Anal. calcd. for $C_{17}H_{14}N_2O_5S$: C, 56.98; H, 3.94; N, 7.82; S, 8.95. Found: C, 56.75; H, 3.66; N, 7.53; S, 8.89%.

Preparation C. t-Butyl
7-phthalimido-3-methyl-3-cephem-4-carboxylate.

A mixture of 13.76 g. (40 mmol.) of 7-phthalimido-3-methyl-3-cephem-4-carboxylic acid, 10 ml. of conc. $H_2SO_4$, 100 ml. of dry dioxane and 50 ml. of liquid isobutylene was stirred at room temperature in a sealed pressure bottle and then poured into an excess of ice cold aqueous $NaHCO_3$( 44 g.). Extraction of the resulting mixture with ethyl acetate and evaporation of the solvent gave a crude ester which was crystallized from CHCl$_3$. The first crop gave 3.34 g. of crystals, m.p. 189°–191°, and the second crop 1.72 g., m.p. 181°–183°; $[\alpha]_D$ = 77.7° (MeCN); ir (CHCl$_3$) 1800, 1785, and 1735 cm$^{-1}$; nmr (CDCl$_3$) δ 1.55 (s, 9, t-Bu); 2.23 (s, 3, CH$_3$), 3.05 and 3.6 (ABq, 2, J = 16 Hz), 5.1 (d, 1, J = 4.5 Hz), 5.72 (d, 1, J = 4.5 Hz) and 7.8 (m, 4, ArH).

Anal. calcd. for: $C_{20}H_{20}N_2O_5S$: C, 59.99; H, 5.03; N, 7.00; O, 19.98; S, 8.01. Found: C, 60.27; H, 4.91; N, 7.04; O, 20.06; S, 7.74%.

Preparation D. t-Butyl 7-phthalimido-3-acetoxymethyl-3-cephem-4-carboxylate and t-butyl 7-(2-carboxybenzamido)-3-acetoxy-3-cephem-4-carboxylate.

A mixture of 3.28 g. (10 mmol.) of t-butyl 7-aminocephalosporanate (7-ACA), 1.5 g. (10 mmol.) of phthalic anhydride and 25 ml. of benzene was refluxed for 2 hrs. using a Dean-Stark water collector. The solution was cooled, washed with $NaHCO_3$ (1.68 g. in 20 ml. of $H_2O$), water, and brine, and then dried. The solvent was evaporated to give 1.22 g. of a neutral product. The product was chromatographed over silica gel using a gradient mixture of benzene and ethyl acetate. Fraction 54–87 gave 330 mg. of the phthalimido compound which was recrystallized from dichloromethane/ether; prisms, m.p. 176°–178°; $[\alpha]_D + 43.4°$ (MeCN); ir ($CHCl_3$) 1800, 1785 and 1735 $cm^{-1}$; $\lambda_{EtOH}$ 260 m$\mu$ ($\epsilon$=10,000); nmr ($CDCl_3$) $\delta$ 1.55 (s, 9, t-Bu); 2.1 (s, 3, $CH_3$), 3.5 (s, 2, $CH_2$); 4.9 and 5.3 (ABq, 2, J = 14 Hz); 5.1 (d, 1, J = 4.5 Hz); 5.82 (d, 1, J = 4.5 Hz), and 7.82 (m, 4, ArH).

Anal. calcd. for: $C_{22}H_{22}N_2O_7S$: C, 57.63; H, 4.84; N, 6.11; O, 24.43; S, 6.99. Found: C, 57.56; H, 4.60; N, 6.31; O, 24.60; S, 6.90%.

After removal of the neutral product the aqueous portion was acidified to pH 3.6 and the acid mixture was extracted with ethyl acetate. Evaporation of the ethyl acetate gave 2.9 g. of t-butyl 7-(2-carboxybenzamido) cephalosporanate. This material was dissolved in 50 ml. of benzene, 15 mg. of imidazole was added, and the mixture was refluxed for 30 min. using a Dean-Stark water collector. After work up procedure and chromatography, 430 mg. of t-butyl 7-phthalimido cephalosporanate was obtained.

The ratio of products from the condensation of phthalic anhydride and the t-Bu ester of 7-ACA depends upon the particular reaction time. If the mixture were heated for only 15 min., about 160 mg. of the phthalimido compound and about 4.34 g. of the phthalamic acid compound would have been obtained.

Preparation E. p-Methoxybenzyl 7-phthalimido-3-methyl-3cephem-4-carboxylate.

To a suspension of 13.4 g. (38 mmol.) of 7-phthalimido-3-methyl-3-cephem-4-carboxylic acid in 20 ml. of dioxane and 10 ml. of water were slowly added 3.8 g. of $KHCO_3$. The solution was evaporated to dryness, and 100 ml. of DMF and 8.8 g. of p-methoxybenzyl bromide were added to the potassium salt residue. The mixture was stirred for 2 hrs. and then poured onto 200 g. of ice. The resulting mixture was extracted twice with ethyl acetate. The extract was washed with water and brine, dried, and the solvent was then evaporated. The residue was recrystallized from ethyl acetate. Yield: 4.1 g. of large crystals, m.p. 118°–121°; second crop 1.8 g.; $[\alpha]_D + 41.2°$ (MeCN), ir ($CHCl_3$) 1800, 1785, 1745 and 1735 $cm^{-1}$, nmr ($CDCl_3$) $\delta$ 2.15 (s, 3, $CH_3$); 3.0 and 3.7 (ABq, 2, J = 15 Hz), 3.8 (s, 3, $CH_3$), 5.11 (d, 1, J = 4.5 Hz), 5.28 (s, 2, $CH_2$), 5.75 (d, 1, J = 4.5 Hz), 6.8–7.8 (m, 8).

Anal. calcd. for: $C_{24}H_{20}N_2O_6S$: C, 62.06; H, 4.34; N, 6.03; O, 20.67; S, 6.90. Found: C, 62.15; H, 4.31; N, 6.32; O, 20.88; S, 6.82%.

EXAMPLE 1
7-(2-Carboxybenzamido)-3-methyl-3-cephem-4-carboxylic acid.

To a solution of 7-phthalimido-3-methyl-3-cephem4-carboxylic acid (3.44 g., 10 mmol.) in 70 ml. tetrahydrofuran at 0°C. were added 80 ml. of ice water and $Na_2S$-$9H_2O$ (5.3 g., 22 mmol.). After 20 min. at 0°C. 10 ml. of 1N HCl were added, and the volume of the mixture was reduced in vacuo to ca. 100 ml. The aqueous solution was slurried with ethyl acetate (80 ml.), and the pH was adjusted to 1.0 with conc. HCl. The organic layer was separated, washed with water (60 ml.) and brine (50 ml.), dried over $MgSO_4$, and evaporated to dryness in vacuo to give 2.97 g. (83%) of 7-(2-carboxybenzamido)-3-methyl-3-cephem-4-carboxylic acid as an amorphous solid; ir (KBr) 1772, 1730, 1720 and 1650 $cm^{-1}$; nmr ($DMSO_{d6}$) 2.08 (s, 3, $CH_3$), 3.29 and 3.65 (ABq, 2, J = 19 Hz), 5.18 (d, 1, J =4.5 Hz), 5.76 (dd, 1, J = 4.5 and 8.0 Hz), and 7.4–8.0 $\delta$ (m, 4, ArH).

Anal. calcd. for: $C_{16}H_{14}N_2O_6S$: C, 53.05; H, 3.89; N, 7.73. Found: C, 52.91; H, 4.17; N, 7.52%.

EXAMPLE 2
7-Phthalisoimido-3-methyl-3-cephem-4-carboxylic acid.

To a solution of 7-(2-carboxybenzamido)-3-methyl-3-cephem-4-carboxylic acid (376 mg., 1 mmol.) in 15 ml. of anhydrous tetrahydrofuran at room temperature were added sodium bicarbonate (420 mg., 5 mmol.), and trifluoroacetic anhydride (0.33 ml., 2.25 mmol.). After 10 min. the reaction mixture was filtered, and the filtrate was evaporated to dryness. The product was taken up in about 10 ml. of 5% sodium bicarbonate solution and washed with ethyl acetate (15 ml.). The pH of the aqueous solution was adjusted to 2.4 with 1N HCl in the presence of ethyl acetate (20 ml.). The organic layer was separated, washed with brine (20 ml.), dried over $MGSO_4$, and evaporated to dryness in vacuo giving 7-phthalisoimido-3-methyl-3-cephem-4-carboxylic acid (240 mg., 67%) as a cream colored amorphous solid: m.p. 179°–180° (dec.); ir (KBr) 1818, 1770, 1731 and 1700 $cm^{-1}$; nmr ($D_2O/HCO_3^-$); 2.03 (s, 3, $CH_3$); 3.20 and 3.78 (ABq, 2, H = 18 Hz); 5.44 (d, 1, J = 4 Hz), 5.84 (d, 1, J =4 Hz) and 7.4–8.0$\delta$ (m, 4, ArH).

Anal. calcd. for $C_{16}H_{12}N_2O_5S$: C, 55.81; H, 3.51; N, 8.14; O, 23.23; S, 9.31. Found: C, 55.97; H, 3.62; N, 8.15; O, 23.18; S, 9.12%.

EXAMPLE 3
7-Amino-3-methyl-3-cephem-4-carboxylic acid.

To a suspension of 7-phthalisoimido-3-methyl-3-cephem-4-carboxylate (172 mg., 0.5 mmol.) in tetrahydrofuran (7 ml.) at 0° was added anhydrous hydrazine (.032 ml., 1 mmol.). After 7 min., 1N HCl (2.5 ml.) and water (2.5 ml.) were added. The mixture was heated on a stream bath for 10 min. after which it was cooled and evaporated in vacuo to a volume of ca. 5 ml. The aqueous solution was filtered, and the pH of the filtrate was adjusted to 3.7 with 5% sodium bicarbonate solution. After 15 min. the solution was filtered giving 73 mg. (68%) of 7-amino-3-methyl-3-cephem-4-carboxylate. Spectral data as well as tlc data showed the product to be identical with an authentic sample of 7-ADCA.

EXAMPLE 4

Methyl 7-(2-carboxybenzamido)-3-methyl-3-cephem-4-carboxylate.

To a solution of 2.86 g. (8 mmol.) of methyl 7-phthalimido-3-methyl-3cephem-4-carboxylate in 80 ml. of tetrahydrofuran at 0°C. were added 2.4 g. (10 mmol.) of $Na_2S.9H_2O$ and 32 ml. of ice water. After 7 minutes at 0°C., 10 ml. of 1N HCl were added to the mixture. The volume was reduced in vacuo to about 40 ml., and the resulting aqueous solution was washed with ethyl acetate. The pH of the aqueous layer was adjusted to 4.5 with 1N HCl and then was extracted with ethyl acetate (40 ml.). The ethyl acetate layer was washed with brine (30 ml.), dried over $MgSO_4$, and evaporated to give 1.8 g. of methyl 7-(2-carboxybenzamido)-3-methyl-3-cephem-4-carboxylate as an amorphous colorless solid. Recrystallization from acetone gave an analytical sample; m.p. 182°–184.5° (dec.); ir (KBr) 1768, 1630, 1610 (shoulder) and 1665 $cm^{-1}$; nmr ($CDCl_3/DMSO_{d-6}$) 2.08 (s, 3, $CH_3$), 3.12 3.52 (ABq, 2, J = 17 Hz), 3.8 (s, 3, $CH_3$ ester), 5.06 (d, 1, J = 4.5 Hz), 5.86 (dd, 1, J = 4.5 and J = 8.0 Hz) and 7.4–8.0δ (m, 4, ArH).

Anal. calcd. for $C_{17}H_{16}N_2O_6S$: C, 54.25; H, 4.28; N, 7.44; S, 8.52. Found: C, 53.98; H, 4.18; N, 7.73; S, 8.58.

The pH of the aqueous layer from above was lowered to pH 2.5 with 1N HCl and then was extracted with ethyl acetate (2 × 30 ml.). The ethyl acetate extracts were combined, washed with brine (30 ml.) and dired over dried 4. The ethyl acetate was evaporated in vacuo during which time a colorless crystalline product crystallized. When the volume had been reduced to ca. 10 ml., the solution was filtered giving 190 mg. (6.5%) of 7-(2-carboxybenzamido)-3-methyl-2-cephem-4-carboxylic acid; m.p. 196–198 (dec.); ir (KBr) 1773, 1700, and 1658 $cm^{-1}$; nmr ($DMSO_{d6}$) 1.88 (s, 3, $CH_3$), 4.64 (s, 1, $C_4$-H), 5.15 (d, 1, J = 4.0 Hz), 5.5 (dd, 1, J =4.0 and 8.0 Hz), 6.15 (s, 1, $C_2$-H) and 7.4–8.0δ (m, 4, ArH).

Anal. calcd. for $C_{16}H_{14}N_2O_6S$: C, 53.03; H, 3.89; N, 7.73; S, 8.85. Found: C, 52.76; H, 3.85; N, 7.68; S, 8.77%.

Evaporation of the filtrate from above gave an additional 600 mg. of methyl 7-(2-carboxybenzamido)-3-methyl-3-cephem-4-carboxylate; total yield—80%.

EXAMPLE 5

Methyl 7-phthalisoimido-3-methyl-3-cephem-4-carboxylate.

To a solution of 1.88 g. (5 mmol.) methyl 7-(2-carboxybenzamido)-3-methyl-3-cephem-4-carboxylate in 40 ml. dry dioxane at room temperature were added 1.52 ml. (11 mmol.) triethylamine and 0.81 ml. (5.5 mmol.) trifluoroacetic anhydride. The mixture was stirred at room temperature for 30 min. and then poured into 180 ml. of ice water. After ca. 5 min. the aqueous mixture was filtered, and the collected cream colored product* was dried in vacuo. Recrystallization from acetone gave 1.44 g. (80%) methyl 7-phthalisoimido-3-methyl-3-cephem-4-carboxylate; m.p. 191°–193°; ir (KBr) 1798, 1771, 1730, and 1710 $cm^{-1}$; nmr ($CDCl_3$); 2.19 (s, 3, $CH_3$), 3.19 and 3.60 (ABq, 2, J = 18 Hz); 3.85 (s, 3, $CH_3$ ester); 5.13 (d, 1, J = 4.5 Hz); 5.80 (d, 1, J = 4.5 Hz); and 7.6–8.28 (m, 4H, ArH). *Crude product weighed 1.60 g. and nmr showed no impurities yield of crude product --89%.

Anal. calcd. for: $C_{17}H_{14}N_2O_5S$: C, 56.98; H, 3.94; N, 7.82; O, 22.32; S, 8.95. Found: C, 56.83; H, 3.83; N, 7.81; O, 22.50; S, 8.94%.

EXAMPLE 6

Methyl 7-amino-3-methyl-3-cephem-4-carboxylate hydrochloride.

Anhydrous hydrazine (.053 ml., 97%, 1.6 mmol.) was added to a suspension of methyl 7-phthalisoimido-3-methyl-3-cephem-4-carboxylate (570 mg., 1.6 mmol.) in 15 ml. tetrahydrofuran at 0°C. After 10 min. at 0°C., the mixture was evaporated to dryness in vacuo. The residual product was taken up in a mixture of 3 ml. tetrahydrofuran and 2.3 ml. 1N HCl. The mixture was heated on a steam bath for 5 min. and then allowed to cool slowly to room temperature. Filtration of the mixture gave 210 mg. of a colorless crystalline product identified as diketophthalazine (m.p. 339°–343°). The filtrate (volume about 10 ml. from washing the precipitate) was evaporated in vacuo to a volume of ca. 5 ml. A gummy material which had formed on the walls of the flask was washed with 5 ml. of water and discarded. The washings were combined with the remaining filtrate from above, and the total mixture evaporated to dryness in vacuo to give a light yellow amorphous product (260 mg., 62%). Thin layer chromatography showed only minor impurities. An analytical sample was obtained by recrystallization from ethanol/diethyl ether; m.p. 173°–179°(dec.); ir (KBr) 1770 and 1734 $cm^{-1}$; nmr ($DMSO_{d-6}$), 2.18 (s, 3, $CH_3$), 3.62 (broad s, 2, methylene), 3.78 (s, 3, $CH_3$ ester), 5.06 (d, 1, J = 4.5 Hz) and 5.21 δ (d, 1, J =4.5 Hz).

Anal. calcd. for: $C_9H_{13}N_2O_3SCl$: C, 40.82; H, 4.95; N, 10.58; S, 12.11; Cl, 13.39. Found: C, 40.83; H, 4.78; N, 10.84; S, 12.05; Cl, 13.49%.

The corresponding free amine was prepared by adjusting the pH of an aqueous solution of the prepared hydrochloride to 8.0 with sodium bicarbonate and extracting the solution with ethyl acetate. The ethyl acetate solution was dried over $MgSO_4$ and evaporated to dryness to give a light yellow resinous product identified as methyl 7-amino-3-methyl3-cephem-4-carboxylate; nmr ($CDCl_3$), 2.11 (s, 3, $CH_3$), 2.54 (broad s, 2, $NH_2$), 3.13 and 3.56 (ABq, 2, J = 18 Hz), 3.83 (s, 3, $CH_3$ ester), 4.69 (d, 1, J = 4.6 Hz) and 4.93 δ (d, 1, J = 4.6 Hz).

EXAMPLE 7 t-Butyl 7-(2-carboxybenzamido)-3-acetoxymethyl-3-cephem-4-carboxylate.

A solution of 458 mg. (1 mmol.) of t-butyl 7-phthalimido-3-acetoxymethyl-3-cephem-4-carboxylate in 10 ml. of THF was cooled in an ice water bath, and 1.1 ml. of 1N NaOH were then added. After stirring for 5 min., 10 ml. of water and 30 ml. of ethyl acetate were added. The ethyl acetate layer was separated, and 70 mg. of starting material were recovered therefrom. The aqueous layer was acidified to pH 4.0, and the acidified layer was extracted with ethyl acetate. After workup, 330 mg. (83%) of the desired phthalamic acid were obtained [α] + 26.37 (MeCN); EtOH 260 mμ (ε 8800); ir ($CHCl_3$) 1785, 1730 and 1685 $cm^{-1}$; nmr ($CDCl_3$) δ 1.55 (s, 9, t-Bu), 2.05 (s, 3, Ac), 3.3 and 3.6

(ABq, 2, J = 17 Hz), 4.72 and 5.2 (ABq, 2, J = 14 Hz), 4.98 (d, 1, J = 4.5 Hz), 5.9 (dd, 1, J = 4.5 and 9 Hz), and 7.5–8 (m, 4, ArH).

EXAMPLE 8 t-Butyl 7-phthalisoimido-3-acetoxymethyl-3-cephem-4-carboxylate.

A solution of 476 mg. (1 mmol.) of t-butyl 7-(2-carboxybenzamido)-3-acetoxymethyl-3-cephem-4-carboxylate and 0.14 ml. (1 mmol.) of triethylamine in 10 ml. of dry THF was cooled to −20°C., and 0.1 ml. of ethyl chloroformate was then added. The mixture was stirred for 20 min. at −20° and for 10 min. at room temperature. The solvent was then evaporated, and the residue was dissolved in $CHCl_3$. The solution was washed with $NaHCO_3$ solution, water and brine. The solution then was dried, and the solvent was evaporated to give 365 mg. of the iso-imide.

EXAMPLE 9 t-Butyl 7-amino-3-acetoxymethyl-3-cephem-4-carboxylate.

A solution of 916 mg. (2 mmol.) of t-butyl 7-phthalisoimido-3-acetoxymethyl-3-cephem-4-carboxylate in 15 ml. of dry THF was cooled in an ice water bath, and 0.078 ml. of anhydrous hydrazine was then added. The mixture was stirred for 5 min., concentrated to a volume of 5 ml., and then 3 ml. of 1N HCl was added. The mixture was refluxed for 2–3 min. and then cooled to room temperature. The precipitated diketophthalazine was filtered, and the filtrate was evaporated to dryness yielding 410 mg. (55%) of the hydrochloride salt, which was converted to the free amine by treatment with $NaHCO_3$ and extraction with chloroform. M.p., ir and nmr spectra were in agreement with an authentic sample prepared according to the method of R. J. Stedman, J. Med. Chem., (1966) p. 444.

EXAMPLE 10 t-Butyl 7-(2-thienylacetamido)-3-acetoxymethyl-3-cephem-4-carboxylate.

A solution of 1.37 g. (3 mmol.) of t-butyl 7-phthalisoimido-3-acetoxymethyl-3-cephem-4-carboxylate in 10 ml. of dry THF was cooled in an ice water bath, and 0.12 ml. of anhydrous hydrazine was added. After the mixture was stirred for 5 min., 0.75 ml. of 2-thienylacetyl chloride was added, and the mixture was refluxed for 8 min., cooled and evaporated to dryness. The residue was dissolved in ethyl acetate, and the solution was washed successively with $NaHCO_3$ solution, 1N HCl, water and brine. The crude mixture was chromatographed over silica gel using a gradient mixture of benzene and ethyl acetate. Fractions 16–73 were collected giving 340 mg. of t-butyl ester of cephalothin $[\alpha]_D$ + 40.0° (MeCN); $\lambda_{EtOH}$ 238 and 262 m$\mu$ ($\epsilon$ 14,200 and 8300); ir ($CHCl_3$) 1785, 1740, 1730 and 1690 $cm^{-1}$; nmr ($CDCl_3$) $\delta$ 1.55 (s, 9, t-Bu), 2.1 (s, 3, $CH_3$), 3.25 and 3.6 (ABq, 2, J = 17 Hz), 3.82 (s, 2, $CH_2$), 4.75 and 5.14 (ABq, 2, $CH_2$), 4.92 (d, 1, J = 4.5 Hz), 5.82 (dd, 1, J = 4.5 and 9 Hz), and 7.2 (m, 3, ArH).

Anal. calcd. for: $C_{20}H_{24}N_2O_6S_2$:
C, 53.08; H, 5.35; N, 6.19; O, 21.21; S, 14.17.

Found: C, 52.84; H, 5.10; N, 6.30; O, 21.46; S, 13.92%.

EXAMPLE 11 t-Butyl 7-(2-carboxybenzamido)-3-methyl-3-cephem-4-carboxylate.

A solution of 800 mg. (2 mmol.) of t-butyl 7-phthalimido-3-methyl-3-cephem-4-carboxylate in 25 ml. of tetrahydrofuran and 8 ml. of water was cooled in an ice bath. To the solution 660 mg. of $Na_2S.9H_2O$ were added, and the mixture was stirred and cooled for 10 min. At the end of this period 10 ml. of water were added, and the mixture was extracted with 40 ml. of ethyl acetate. The extract was discarded. The aqueous portion was acidified to pH 4.3 with 1N $H_2SO_4$ and then extracted with ethyl acetate. The ethyl acetate extract was dried and evaporated, giving 700 mg. of the title compound. The product was recrystallized from chloroform/cyclohexane; m.p. 178°–179°; ir (nujol) 1770, 1735, and 1680 $cm^{-1}$; nmr ($CDCl_3$ + $DMSO_{d6}$) $\delta$ 1.5 (s, 9, t-BU), 2.1 (s, 3, $CH_3$), 3.2 and 3.5 (ABq, 2, J = 18 Hz), 5.02 (d, 1, J = 4.5 Hz), 5.82 (dd, 1, J = 4.5 and 9Hz), and 7.4–8 (m, H, ArH).

Anal. Calcd. for $C_{20}H_{22}N_2O_6S$:
C, 57.40; H, 5.30; N, 6.69; O, 22.94 and S, 7.66.
Found: C, 57.70; H, 5.20; N, 6.52; O, 22.72 and S, 7.53%.

The identical (nmr, ir, m.p.) substance also can be obtained in 94% yield from phthalic anhydride and the t-butyl ester of 7-ADCA.

EXAMPLE 12 t-Butyl 7-phthalisoimido-3-methyl-3-cephem-4-carboxylate.

A mixture of 4.18 g. (10 mmol.) of t-butyl 7-(2-carboxybenzamido)-3-methyl-3-cephem-4-carboxylate, 40 ml. of dry tetrahydrofuran (THF) and 1.39 ml. (10 mmol.) of triethylamine was cooled in an ice-salt bath. A solution of 1.0 ml. (10.5 mmol.) of ethyl chloroformate in 10 ml. of dry THF was added, and the mixture was stirred and cooled for 20 min. The mixture was warmed to room temperature, and stirring was continued for an additional 20 min. The precipitated salt ($Et_3N.HCl$) was filtered, the filtrate was evaporated to dryness, and the residue was dissolved in ethyl acetate which was then washed with water and brine. The solution was warmed to boiling, and the solvent was evaporated. The residue (3.93 g. or 98%) is pure iso-imide. A sample (1.0 g.) was recrystallized from acetonitrile (5 ml.) as silky needles (570 mg.) m.p. 179°–180°; $[\alpha]_D$ −128.7° (MeCN); ir (KBr) 1810, 1775, 1730 and 1710 $cm^{-1}$; nmr ($CDCl_3$) $\delta$ 1.55 (s, 9, t-Bu); 2.15 (s, 3, $CH_3$); 3.18 and 3.59 (ABq, 2, J = 18 Hz); 5.15 (d, 1, J = 4.5 Hz); 5.18 (d, 1, J = 4.5 Hz); and 7.65–8.05 (m, 4, ArH).

Anal. Calcd. for: $C_{20}H_{20}N_2O_5S$:
C, 59.96; H, 5.03; N, 7.00; S, 8.01.
Found: C, 59.66; H, 4.74; N, 7.40; and S, 7.87%.

EXAMPLE 13 t-Butyl 7-amino-3-methyl-3-cephem-4-carboxylate.

A solution of 400 mg. (1 mmol.) of t-butyl 7-phthalisoimido-3-methyl-3-cephem-4-carboxylate in 15 ml. of dry THF was cooled in an ice-water bath. The solution was stirred, and 0.04 ml. of anhydrous hydrazine was added; stirring was continued for 5 min. The mixture was then acidified by addition of 2.5 ml. of 1N HCl. After a brief period of reflux, a major portion of the THF was evaporated on a rotavapor. Diketophthalazine precipitated and was filtered, washed with 10 ml. of water, again filtered, and the filtrate was evaporated to dryness. The residual hydrochloride salt (270 mg. or 88%), using ethyl acetate and sodium bicarbonate, was converted to the free amino ester, a colorless solid: m.p. 118°–120°; $[\alpha]_D$ + 76.8°(MeCN); $\lambda_{max}$ (EtOH) 268 m$\mu$ ($\epsilon$ 6350), ir (CHCl$_3$) 1790 and 1735 cm$^{-1}$; nmr (CDCl$_3$) $\delta$ 1.52 (s, 9, t-Bu), 2.1 (s, 3, CH$_3$), 3.17 and 3.64 (ABq, 2, J = 18 Hz) and 4.7 (d, 1, J = 4.5 Hz), and 4.93 (d, 1, J = 4.5 Hz).

anal. calcd. for: $C_{12}H_{18}N_2O_3S$:
C, 53.31; H, 6.71; N, 10.36; O, 17.75; S, 11.86.
Found: C, 53.35; H, 6.45; N, 10.12; O, 18.05 and S, 12.09%.

EXAMPLE 14 p-Methoxybenzyl 7-(2-carboxybenzamido)-3-methyl-3-cephem-4-carboxylate.

A solution of 930 mg. (2 mmol.) of p-methoxybenzyl 7-phthalimido-3-methyl-3-cephem-4-carboxylate in 25 ml. of THF and 8 ml. of water was cooled in an ice water bath, and 660 mg. of Na$_2$S.9H$_2$O were then added. The mixture was stirred for 15 min., and 10 ml. of water and 40 ml. of ethyl acetate were added. The layers were separated, and 140 mg. of a neutral material were obtained from the ethyl acetate layer. The aqueous layer was acidified to pH 4.3 with 1N H$_2$SO$_4$ and extracted twice with ethyl acetate. The ethyl acetate extract was washed, dried, and evaporated to give 660 mg. (68%) of the phthalamic acid as an amorphous solid, $[\alpha]_D$ + 85.6° (MeCN); ir (CHCl$_3$), 1781, 1740 and 1710 cm$^{-1}$; nmr (CDCL$_3$) $\delta$ 2.08 (s, 3, CH$_3$), 3.1 and 3.43 (ABq, 2, J = 17 Hz), 3.79 (s, 3, CH$_3$), 5.0 (d, 1, J = 4.5 Hz), 5.1 (s, 2, CH$_2$), 5.8 (dd, 1, J = 4.5 Hz, 6.75–7.6 (m, 8).

Anal. calcd. for $C_{24}H_{22}N_2O_7S$:
C, 59.74; H, 4.60; N, 5.81; O, 23.21; S, 6.65.
Found: C, 59.81; H, 4.32; N, 6.07; O, 23.34; S. 6.51%.

EXAMPLE 15 p-Methoxybenzyl 7-phthalisoimido-3-methyl-3-cephem-4-carboxy-late.

A mixture of 400 mg. (0.8 mmol.) of p-methoxybenzyl 7-(2-carboxybenzamido)-3-methyl-3-cephem-4-carboxylate, 15 ml. of dry THF and 0.110 ml. of triethylamine was cooled with an ice-salt bath, and 0.08 ml. of ethyl chloroformate was added. The mixture was stirred and cooled for 25 min. The precipitated salt of Et$_3$N.HCl was filtered. The filtrate was evaporated to dryness, and the residue was dissolved in chloroform and, after washing and drying, 300 mg. of an amorphous solid product was collected. $\lambda_{max}$ (EtOH) 265 m$\mu$ ($\epsilon$ 8800), ir (CHCl$_3$) 1820, 1785, 1735, and 1715 cm$^{-1}$, nmr (CDCl$_3$) $\delta$ 2.15 (s, 3, CH$_3$), 3.15 and 3.55 (ABq, 2, J = 18 Hz), 4.00 (s, 3, CH$_3$), 5.18 ($\alpha$, 1, J = 4.5 Hz), 5.3 (s, 2, CH$_2$), 5.78 (d, 1, J = 4.5 Hz), and 6.8–8 (m, 8, ArH).

Anal. calcd. for: $C_{24}H_{20}N_2O_6S$:
C, 62.06; H, 4.34; N, 6.03; O, 20.67; S, 6.90.
Found: C, 62.18; H, 4.34; N, 6.26; O, 20.66; and S, 6.98%.

EXAMPLE 16 p-Methoxybenzyl 7-amino-3-methyl-3-cephem-4-carboxylate, p-toluene sulfonic acid salt.

To a solution of 190 mg. (0.4 mmol.) of p-methoxybenzyl 7-phthalisoimido-3-methyl-3-cephem-4-carboxylate in 10 ml. of dry THF, 0.017 ml. of anhydrous hydrazine was added at room temperature. The mixture was stirred for 5 min. and evaporated to dryness. The residue was dissolved in 2.0 ml. of 75% aqueous acetonitrile, and 90 mg. of p-toluenesulfonic acid monohydrate were added. The mixture was refluxed, and diketophthalazine started to precipitate. The mixture was cooled to room temperature, and the precipitate was filtered. The filtrate was evaporated, and the residue was triturated with ether. Yield: 190 mg. of the title compound. This material is identical with the salt described by Chauvette et. al., J. Org. Chem., 36, 1265 (1971).

EXAMPLE 17 p-Nitrobenzyl 7-(2-carboxybenzamido)-3-methyl-3-cephem-4-carboxylate.

To an ice cooled solution of 480 mg. (1 mmol.) of p-nitrobenzyl 7-phthalimido-3-methyl-3-cephem-4-carboxylate in 25 ml. of tetrahydrofuran and 5 ml. of water were added 340 mg. of sodium sulfide (Na$_2$S.9-H$_2$O). The mixture was stirred at pH 11.5 for 7 min., and 40 ml. of ethyl acetate and 10 ml. of water were added. The layers were separated, and the organic layer was washed with 5 ml. of water and 5 ml. of brine to give 150 mg. of a neutral material. The aqueous layer was acidified to pH 4.5 with 1N sulfuric acid, and the resulting emulsion was extracted with 25 ml. of ethyl acetate. The extract was washed with brine, dried and evaporated to dryness to give 290 mg. of the crude product, from which 150 mg. (30%) of pure product was obtained.

The same compound also can be prepared by the alternate procedure of refluxing phthalic anhydride and the p-nitrobenzyl ester of 7-ADCA in acetonitrile for 30 min.

A sample was recrystallized from dioxane/water, and colorless crystals were obtained melting at 192°–193°; nmr (DMSO-d$_6$) $\delta$ 2.04 (s, 3, CH$_3$), 3.35 and 3.68 (ABq, 2, J = 18 Hz), 5.2 (d, l, J = 4 Hz, H-6), 5.4 (s, 2, CH$_2$), 5.8 (d, d, l, J = 4.5 and 9 Hz), 8 (m, 8 ArH).

Anal. Calcd. for $C_{23}H_{19}N_3O_8S$: C, 55.53; H, 3.85; N, 8.45; O, 25.73; S, 6.45. Found: C, 55.67; H, 3.94; N, 8.49; O, 25.89; S, 6.47%.

The subsequent acidification of the aqueous solution to pH 2.0 followed by ethyl acetate extraction produced 120 mg. of p-nitrobenzyl 7-(2-carboxybenzamido)-3-methyl-2-cephem-4-carboxylate.

EXAMPLE 18 p-Nitrobenzyl 7-phthalisoimido-3-methyl-3-cephem-4-carboxylate.

A. Using ethyl chloroformate. p-Nitrobenzyl 7-(2-carboxybenzamido)-3-methyl-3-cephem-4-carboxylate (10 g., 20 mmol.) and 2.8 ml. (20 mmol.) of triethylamine were dissolved in 200 ml. of dry THF. While the mixture was stirred and cooled at ice bath temperature, 2.0 ml. (20 mmol.) of ethyl chloroformate were added.

The stirring was continued for 20 min. in an ice bath and for 10 min. at room temperature. The salt (Et$_3$N.HCl) was filtered, and the filtrate was evaporated to dryness. Yield: 4.6 g. of crude product. The product was recrystallized from acetonitrile as long colorless needles, m.p. 204°–205°; ir (KBr) 1821, 1785, 1730 and 1710 cm$^{-1}$.

Anal. calcd. for: C$_{23}$H$_{17}$N$_3$O$_7$S: C, 57.62; H, 3.57; N, 8.76; O, 23.36; S, 6.69. Found: C, 57.42; H, 3.53; N, 8.99; O, 23.64; S, 6.66%.

B. Using trifluoroacetic anhydride. A solution of 1.0 g. (2 mmol.) of p-nitrobenzyl 7-(2-carboxybenzamido)-3-methyl-3-cephem-4-carboxylate and 0.34 ml. (2.6 mmol.) of triethylamine in 25 ml. of dioxane was cooled in an ice-water bath. While the mixture was stirred, 0.36 ml. (2.6 mmol.) of trifluoroacetic anhydride was added. Stirring was continued for 30 min., and 10 ml. of water were added. The iso-imide precipitated and was filtered and dried. Yield: 840 mg. (87%). The product was identical (ir, m.p.) to the material prepared by method A.

EXAMPLE 19 p-Nitrobenzyl 7-amino-3-methyl-3-cephem-4-carboxylate, hydrochloride salt

A solution of 960 mg. (2 mmol.) of p-nitrobenzyl 7-phthalisoimido-3-methyl-3-cephem-4-carboxylate in 30 ml. of dry THF was cooled in an ice-water bath, and 0.075 ml. of anhydrous hydrazine was added. The mixture was stirred for 5 min., and then about 20 ml. of the solvent was evaporated on a rotavapor. About 4 ml. of 1N HCl was added to the resulting mixture, and the mixture was heated on a steam bath for 5 min. The warm mixture was left at room temperature for 30 min., after which the precipitated diketophthalazine (m.p. 340°–343°) was filtered. The filtrate was evaporated to dryness giving 750 mg. (98%) of the hydrochloride salt of 7-ADCA p-nitrobenzyl ester.

EXAMPLE 20 p-Nitrobenzyl 7-phenylacetamido-3-methyl-3-cephem-4-carboxylate

To a suspension of p-nitrobenzyl 7-phthalisoimido-3-methyl-3-cephem-4-carboxylate (480 mg., 1 mmol.) in tetrahydrofuran at 0°C. was added anhydrous hydrazine (.033 ml., 1.06 mmol.). After ten minutes the mixture was evaporated to dryness. The residue was taken up in acetone (15 ml.) and tetrahydrofuran (15 ml.), and phenylacetyl chloride (.28 ml., 2.2 mmol.) was added. After refluxing for 30 min., the mixture was cooled and evaporated in vacuo to dryness. The product was taken up in chloroform (50 ml.) and washed successively with 1N HCl (30 ml.), 10% sodium bicarbonate (40 ml.), and brine (40 ml.), dried over MgSO$_4$, and evaporated in vacuo to dryness. The colorless product was slurried with ethyl acetate (12 ml.). Filtration gave p-nitrobenzyl 7-phenylacetamido-3-methyl-3-cephem-4-carboxylate (280 mg., 60%). Recrystallization from ethyl acetate gave an analytical sample: m.p. 227°–230°; ir (KBr) 1772, 1732 and 1652 cm$^{-1}$; nmr (CDCl$_3$/DMSO$_{d-6}$) 2.17 (s, 3, CH$_3$), 3.23 and 3.54 (ABq, 2, J = 17 Hz), 3.62 (s, 2, side chain CH$_2$), 4.98 (d, 1, J = 4.5 Hz), 5.39 (s, 2, ester CH$_2$), 5.60 (dd, 1, J = 4.5 and 8.0 Hz), 7.34 (s, 5, ArH) and 7.90 (m, 4, ArH).

Anal. calcd. for: C$_{23}$H$_{21}$N$_3$O$_6$S: C, 59.09; H, 4.53; N, 8.99; O, 20.53; S, 6.86. Found: C, 58.92; H, 4.24; N, 9.21; O, 20.40; S, 6.64

EXAMPLE 21 t-Butyl 7-(3'-carboxy)acrylamido-3-acetoxymethyl-3-cephem-4-carboxylate

A solution of 656 mg. (2 mmol.) of t-butyl 7-amino-3-acetoxymethyl-3-cephem-4-carboxylate and 196 mg. (2 mmol.) of maleic anhydride in 20 ml. benzene was refluxed for ½ hour, cooled, and evaporated in vacuo to dryness. Tlc indicated no starting material and one slow moving product: nmr (CDCl$_3$) 94 (s, 9, t-Bu), 127 (s, 3, OAc), 207 and 216 (ABq, 2, J=20 Hz), 293 and 307 (ABq, J=14.0, CH$_2$OAc), 305 (1, d, J=4.5, acetidinone H), 350 (1, q, J=4.5 and 8.0 Hz, azetidinone H), 390 (2H, q, J=12 and 2.0 Hz), 534 (1, d, J=8.0, NH), and 806 Hz (1, broad s, COOH).

EXAMPLE 22 t-Butyl 7-isomaleimido-3-acetoxymethyl-3-cephem-4-carboxylate

A. Using N,N'-dicyclohexylcarbodiimide. To a solution of 2.13 g. (5 mmol.) of t-butyl 7-(3'-carboxy)acrylamido-3-acetoxymethyl-3-cephem-4-carboxylate in 150 ml. methylene chloride at room temperature was added 1.02 g. (5 mmol.) N,N'-dicyclohexylcarbodiimide. The resulting solution was stirred at room temperature for 1 hour, filtered, and the filtrate was evaporated in vacuo to dryness. The product residue was taken up in ethyl acetate (40 ml.) and washed successively with dilute HCl, water, 10% NaHCO$_3$ solution, and brine, and dried over MgSO$_4$. Evaporation of the mixture in vacuo gave a brown foam (1.85 g.). The nmr spectrum (CDCl$_3$) indicated a clean sample of t-butyl 7-isomaleimido-3-acetoxymethyl-3-cephem-4-carboxylate; 93 (9, s, t-Bu), 125 (3, s, OAc) 204 and 216 (2, ABq, J=18 Hz), 291 and 305 (2, ABq, J=14 Hz, CH$_2$OAc), 306 (1, d, J=4.5 Hz), 346 (1, d, J=4.5 Hz, azetidinone H), 405 and 444 (2, d, J=6 Hz isomaleimide H). B. Using trifluoroacetic anhydride. To a solution of 852 mg. (2 mmol.) of t-butyl 7-(3'-carboxy)acrylamido-3-acetoxymethyl-3-cephem-4-carboxylate in 25 ml. tetrahydrofuran at room temperature were added 0.28 ml. (2 mmol.) triethylamine followed by 0.30 ml. (2 mmol.) trifluoroacetic anhydride. After 20 minutes at room temperature the reaction mixture was evaporated in vacuo to dryness. The crude product was taken up in 20 ml. ethyl acetate and washed successively with water, 10% NaHCO$_3$, and brine, and then dried over MgSO$_4$. Evaporation in vacuo gave 530 mg. of a brown foam identified as t-butyl 7-isomaleimido-3-acetoxymethyl-3-cephem-4-carboxylate: nmr (CDCl$_3$) 93 (9, s, t-Bu), 125 (3, s, OAc), 204 and 216 (2, ABq, J=18 Hz), 291 and 305 (2, ABq, J=14 Hz, CH$_2$OAc), 306 (1, d, J=4.5 Hz), 346 (1, d, J=4.5 Hz, azetidinone H), and 405 and 444 (2, d's, J=6 Hz, isomaleimide H).

EXAMPLE 23 t-Butyl 7-amino-3-acetoxymethyl-3-cephem-4-carboxylate.

To a solution of 408 mg. (1 mmol.) of t-butyl 7-isomaleimido-3-acetoxymethyl-3-cephem-4-carboxylate in 15 ml. of tetrahydrofuran at 0°C. was added 0.032 ml. (1 mmol.) of anhydrous hydrazine. After 10 min. at 0°C. the reaction mixture was evaporated to dryness. The residue was dissolved in a mixture of 4 ml. of tetrahydrofuran and 2.5 ml. of 1N HCl, and the mixture was warmed on a steam bath for about 3 minutes. After allowing the mixture to stand at room temperature for ½ hour, the tetrahydrofuran was removed in vacuo, and 10 ml. of water were added. The acidic aqueous layer was washed with ethyl acetate (2 × 10 ml.). Ethyl acetate (15 ml.) was added, and the pH of the aqueous layer was adjusted to 8.0 with NaHCO$_3$. The organic layer was separated, washed with brine, and dried over MgSO$_4$. Evaporation in vacuo gave 75 mg. of a tan colored amorphous product. The nmr and tlc data showed the product to be identical to authentic t-butyl 7-amino-3-acetoxymethyl-3-cephem-4-carboxylate.

EXAMPLE 24

Benzhydryl 6-(2'-carboxybenzamido)penicillinate.

To a solution of benzhydryl 6-phthalimido penicillinate (2.56 g., 5 mmol.) in 50 ml. tetrahydrofuran at 0°C. were added 1.35 g. (~5.5 mmol.) Na$_2$S.9H$_2$O and 50 ml. ice water. After 10 minutes at 0°C., 5 ml. of 1.0 N HCl were added, and the volume of the mixture was reduced in vacuo to ~50 ml. and washed with two 50 ml. portions of ethyl acetate. The pH of the aqueous layer was adjusted to 4.0 with conc. HCl and then extracted with 50 ml. ethyl acetate. The ethyl acetate layer was washed with brine and dried over MgSO$_4$. Evaporation in vacuo gave benzhydryl 6-(2'-carboxybenzamido)penicillinate as a colorless foam: nmr (CDCl$_3$) 73 (3, s), 92 (3, s), 269 (1, s, H-3), 335–355 (2, m, azetidinone H), 413 (1, s, (C$_6$H$_5$)$_2$CH), and 430–480 Hz (14, m, ArH).

EXAMPLE 25

Benzhydryl 6-phthalisoimido penicillinate

A. Using trifluoroacetic anhydride. To a solution of 530 mg. (1 mmol.) of benzhydryl 6-(2'-carboxybenzamido)penicillinate in 10 ml. dry dioxane were added 0.14 ml. (1 mmol.) of triethylamine and 0.15 ml. (1 mmol.) of trifluoroacetic anhydride. After 10 minutes at room temperature the yellow reaction mixture was poured into 50 ml. of ice water (plus about 20 g. ice). After the ice in the aqueous mixture melted, the light yellow precipitate was filtered giving 290 mg. (after drying) of a yellow amorphous solid. The nmr spectrum was consistent for benzhydryl 6-phthalisoimido penicillinate: nmr (CDCl$_3$) 77 (3, s), 99 (3, s), 278 (1, s, H-3), 342 (2, q, J=4.0, azetidinone H), 420 (1, s, (C$_6$H$_5$)$_2$CH) and 430-490 (14, m, ArH).

B. Using N,N'-dicyclohexylcarbodiimide. To a solution of 265 mg. (0.5 mmol.) benzhydryl 6-(2'-carboxybenzamido)penicillinate in 7 ml. of methylene chloride were added 102 mg. (0.5 mmol.) of N,N'-dicyclohexylcarbodiimide. After ½ hour at room temperature the reaction mixture was filtered, and the filtrate was evaporated in vacuo to dryness. The nmr spectrum showed the crude product to be a clean sample of benzhydryl 6-phthalisoimido penicillinate.

EXAMPLE 26

Benzhydryl 6-amino penicillinate.

To a solution of 1 mmol. benzhydryl 6phthalisoimido penicillinate in 35 ml. of dry tetrahydrofuran at −76°C. was added a solution of 0.053 ml. (1 mmol.) of methylhydrazine in 5 ml. tetrahydrofuran. The solution was then removed from the dry ice-acetone bath and was allowed to warm to room temperature over a 1 hour period. The reaction mixture was evaporated in vacuo to dryness, and the product residue was taken up in 15 ml. CHCl$_3$. The mixture was allowed to stand at room temperature for 1 hour during which time methylphthalhydrazide (mp 243°–245°C.) precipitated. Filtration and evaporation in vacuo of the filtrate gave a light colored foam which was taken up in 20 ml. of ethyl acetate and extracted twice with 10 ml. of 0.05 N HCl. The aqueous acidic extracts were combined and added dropwise to a stirred slurry of 25 ml. of ethyl acetate and 25 ml. of 10% NaHCO$_3$ solution. The organic layer was separated, washed with brine, and dried over MgSO$_4$. Evaporation gave a colorless foam. Thin-layer chromatography (tlc) and the nmr spectrum of the foam are consistent with the structure of the title compound.

EXAMPLE 27

6-phthalisoimido penicillanic acid.

A. Using trifluoroacetic anhydride. To a solution of 364 mg. (1 mmol.) of 6-(2'-carboxybenzamido)-penicillanic acid in 15 ml. dry dioxane at room temperature were added 0.42 ml. (3 mmol.) of triethylamine followed by 0.30 ml. (2 mmol.) of trifluoroacetic anhydride. After 15 minutes the yellow reaction mixture was poured into a mixture of 50 ml. of water, 20 g. of ice and 0.07 ml. (.5 mmol.) of triethylamine. The finely divided precipitate which formed was filtered, washed with water, and dried in vacuo to give 190 mg. of a light yellow amorphous solid. The nmr spectrum indicated traces of 6-phthalimido penicillanic acid, but the major product was identified as 6-phthalisoimido penicillanic acid: nmr (CDCl$_3$) 99 (3, s), 104 (3, s), 277 (1, s, H-3), 344 (2, q-like singlet, azetidinone H), and 472 Hz (4, m, ArH).

B. Using N,N'-dicyclohexylcarbodiimide. To a solution of 1.45 g. (4 mmol.) of 6-(2'-carboxybenzamido)-penicillanic acid in 40 ml. of methylene chloride were added 1.0 g. (4 mmol.) of N,N'-dicyclohexylcarbodiimide. After ½ hour at room temperature the reaction mixture was filtered, and the filtrate was evaporated in vacuo to dryness. The nmr spectrum indicated a 3:1 mixture of the phthalisoimide and the phthalimide, respectively.

EXAMPLE 28 p-Methoxybenzyl 6-(2'-carboxybenzamido)penicillinate

To a solution of p-methoxybenzyl 6-phthalimido penicillinate )2.33 g., 5 mmol.) in 50 ml. tetrahydrofuran at 0°C. were added 1.35 g. (~5.5 mmol.) of Na$_2$S.9-H$_2$O and 50 ml. of ice water. After 12 minutes at 0°C., 5 ml. of 1.0 N NCl were added, and the volume of the mixture was reduced in vacuo to about 50 ml. The mixture was washed with two 50 ml. portions of ethyl acetate. The pH of the aqueous layer was adjusted to 4.1 with conc. HCl and then was extracted with 35 ml. ethyl acetate. The ethyl acetate extract was washed with brine and dried over MgSO$_4$. Evaporation in vacuo to dryness gave 2.35 grams of p-methoxybenzyl 6-(2'-carboxybenzamido)penicillinate as a colorless foam: nmr (CDCl$_3$) 82 (3, s), 92 (3, s), 227 (3, s, OMe), 263 (1, s, H-3), 305 (2, s, CH$_2$), 330–350 (2, m, β-lactam H), 400–480 (8, m, ArH), and 630 Hz (1, broad s, COOH).

EXAMPLE 29 p-Methoxybenzyl 6-phthalisoimido penicillinate.

Ethyl chloroformate (0.2 ml., 2 mmol.) was added to a solution of p-methoxybenzyl 6-(2'-carboxybenzamido)penicillinate (968 mg., 2 mmol.) and triethylamine (0.27 ml., 2 mmol.) in 15 ml. of tetrahydrofuran at 0°C. After 15 min. at 0°, the mixture was allowed to warm to room temperature, filtered, and the filtrate evaporated in vacuo to dryness. The crude product was taken up in 20 ml. ethyl acetate and was washed successively with 10% $NaHCO_3$, water, and brine. After drying over $MgSO_4$, the ethyl acetate solution was evaporated in vacuo to dryness to give p-methoxybenzyl 6-phthalisoimido penicillinate as a light yellow foam: nmr ($CDCl_3$) 84 (3, s), 98 (3, s), 230 (3, s, OMe), 271 (1, s, 3-H), 309 (2, s, $CH_2$), 338 (2, q, J=4.0 Hz, azetidinone H), 410–490 Hz (8, m, ArH).

EXAMPLE 30 p-Methoxybenzyl 6-amino penicillinate.

To a solution of 480 mg. (1 mmol.) of p-methoxybenzyl 6-phthalisoimido penicillinate in 35 ml. of dry tetrahydrofuran at −76°C. was added a solution of 0.053 ml. (1 mmol.) of methylhydrazine in 5 ml. tetrahydrofuran. The solution was then removed from the dry ice-acetone bath and was allowed to warm to room temperature over a 1 hour period. The reaction mixture was evaporated in vacuo to dryness, and the product residue was taken up in 15 ml. $CHCl_3$. The mixture was allowed to stand at room temperature for 1 hour during which time methylphthalhydrazide (mp 243°–245°C.) precipitated. Filtration and evaporation in vacuo of the filtrate gave a light colored form which was taken up in 20 ml. of ethyl acetate and extracted twice with 10 ml. of 0.05 N HCl. The aqueous acidic extracts were combined and added dropwise to a stirred slurry of 25 ml. of ethyl acetate and 25 ml. of 10% $NaHCO_3$ solution. The organic layer was separated, washed with brine, and dried over $MgSO_4$. Evaporation in vacuo gave 200 mg. (60%) of p-methoxybenzyl 6-amino penicillinate as a colorless foam: nmr ($CDCl_3$) 85 (3, s), 97 (3, s), 231 (3, s, $OCH_3$), 266 (1, s, H-3), 274 (1, d, J=4.0 Hz, azetidinone H), 311 (2, s, $CH_2$), 332 (1, d, J=4.0 Hz, azetidinone H) and 410–450 Hz (4, m, ArH); mass spec. m/c 336, $M^+$.

We claim:
1. A process for preparing an isoimide of the formula

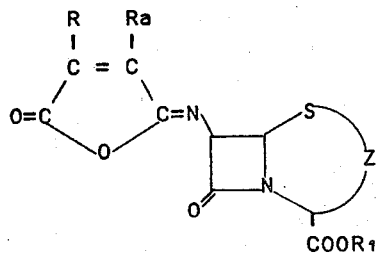

which comprises the step of dehydrating an amic acid of the formula

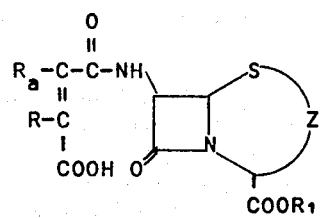

in which, in the above formulae, R and $R_a$ are hydrogen, or R and $R_a$ taken together with the carbon atoms to which they are attached represent an ortho-phenylene ring;

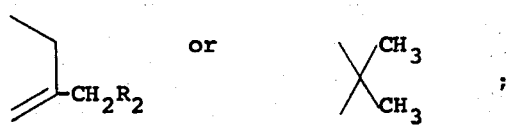

$R_1$ is hydrogen or a carboxy protecting group; and $R_2$ is hydrogen, acetoxy, methoxy, methylthio, (5-methyl-1,3,4-thiadiazol-2-yl)thio, or (1-methyl-1H-tetrazol-5-yl)thio.

2. Process of claim 1, in which the amic acid is dehydrated by treatment with N,N'-dicyclohexylcarbodiimide, an alkyl chloroformate and a tertiary amine, or trifluoroacetic anhydride and a tertiary amine.

3. Process of claim 2, in which the amic acid is reacted with N,N'-dicyclohexylcarbodiimide in an inert solvent at a temperature of from about 0°C. to about 30°C.

4. Process of claim 1, in which the amic acid is reacted with trifluoroacetic anhydride in the presence of a tertiary amine at a temperature of from about 0°C. to about 30°C.

5. Process of claim 1, in which the amic acid is treated with an alkyl chloroformate in the presence of a tertiary amine at a temperature of from about −20°C. to about +5°C.

6. Process of claim 1, in which $R_1$ is $C_1$-$C_4$ alkyl, 2,2,2-trichloroethyl, benzyl, p-nitrobenzyl, p-methoxybenzyl, benzhydryl, $C_2$-$C_6$ alkanoyloxymethyl, phenacyl, or p-halophenacyl.

7. Process of claim 1, in which R and $R_a$ are hydrogen.

8. Process of claim 1, in which R and $R_a$ taken together with the carbon atoms to which they are attached represent an ortho-phenylene ring.

9. Process of claim 8, in which Z is

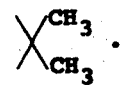

10. Process of claim 8, in which Z is

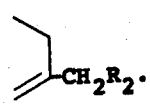

11. Process of claim 10, in which $R_1$ is hydrogen or p-nitrobenzyl.

12. Process of claim 11, in which $R_2$ is hydrogen.

13. Process of claim 11, in which $R_2$ is acetoxy.

14. Process of claim 11, in which $R_2$ is (5-methyl-1,3,4-thiadiazo-2-yl)thio.

15. Process of claim 11, in which $R_2$ is (1-methyl-1H-tetrazol-5-yl)thio.

16. A process for cleaving the isoimido function of an isoimide compound having the formula

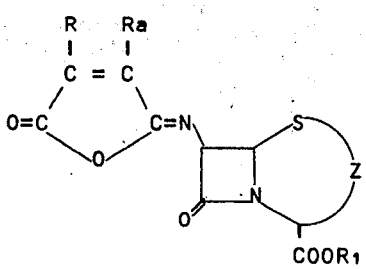

in which R and $R_a$ are hydrogen, or R and $R_a$ taken together with the carbon atoms to which they are attached represent an ortho-phenylene ring;

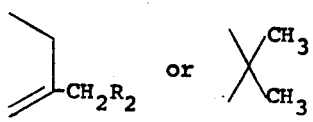

$R_1$ is hydrogen or a carboxy protecting group; and $R_2$ is hydrogen, acetoxy, methoxy, methylthio, (5-methyl-1,3,4-thiadiazol-2-yl)thio, or (1-methyl-1H-tetrazol-5-yl)thio; which comprises the steps of (1) reacting said isoimide compound with a hydrazine of the formula

in which $R_3$ and $R_4$ independently are hydrogen or methyl; and, (2) a) reacting the reaction mixture from the aforementioned hydrazine treatment with an acyl halide to produce the corresponding 7-acylamido cephalosporin or 6-acylamido penicillin; or b. when at least one of $R_3$ and $R_4$ is methyl, recovering the corresponding 7-amino cephalosporin or 6-amino penicillin from the reaction mixture of the aforementioned hydrazine treatment; or c. when $R_3$ and $R_4$ are hydrogen, heating the reaction mixture from the aforementioned hydrazine treatment to a temperature of from about 50°C. to about 100°C. to produce the corresponding 7-amino cephalosporin or 6-amino penicillin; or d. when $R_3$ and $R_4$ are hydrogen, reacting the reaction mixture from the aforementioned hydrazine treatment with acid to produce the corresponding 7-amino cephalosporin or 6-amino penicillin in the form of its acid addition salt.

17. Process of claim 16, in which the isoimide is first reacted with up to 1 equivalent of a hydrazine in which $R_3$ and $R_4$ are hydrogen per equivalent of the isoimide at a temperature of from about −76°C. to about room temperature for from about 1 to about 10 minutes, and the resulting reaction mixture is reacted with from about 1 to about 2 equivalents of an acid selected from the group consisting of hydrochloric acid, hydrobromic acid, phosphoric acid, p-toluenesulfonic acid, methanesulfonic acid, and sulfuric acid per equivalent of the original isoimide for about 5 to about 10 minutes to produce the corresponding amino cephalosporin or penicillin in the form of its acid addition salt.

18. Process of claim 16, in which the isoimide is first reacted with up to 1 equivalent of a hydrazine in which at least one of $R_3$ and $R_4$ is methyl per equivalent of the isoimide at a temperature of from about −76°C. to about room temperature for from about 1 to about 10 minutes to produce the corresponding amino cephalosporin or penicillin.

19. Process of claim 16, in which $R_1$ is $C_1$–$C_4$ alkyl, 2,2,2-trichloroethyl, benzyl, p-nitrobenzyl, p-methoxybenzyl, benzhydryl, $C_2$–$C_6$ alkanoyloxymethyl, phenacyl, or p-halophenacyl.

20. Process of claim 16, in which R and $R_a$ are hydrogen.

21. Process of claim 16, in which R and $R_a$ taken together with the carbon atoms to which they are attached represent an ortho-phenylene ring.

22. Process of claim 21, in which Z is

23. Process of claim 21, in which Z is

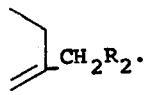

24. Process of claim 23, in which $R_1$ is hydrogen or p-nitrobenzyl.

25. Process of claim 24, in which $R_2$ is hydrogen.

26. Process of claim 24, in which $R_2$ is acetoxy.

27. Process of claim 24, in which $R_2$ is (5-methyl-1,3,4-thiadiazo-2-yl)thio.

28. Process of claim 24, in which $R_2$ is (1-methyl-1H-tetrazol-5-yl)thio.

29. A process for cleaving the amic acid function of a compound having the formula

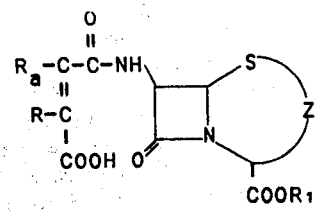

in which R and $R_a$ are hydrogen, or R and $R_a$ taken together with the carbon atoms to which they are attached represent an ortho-phenylene ring; Z is

$R_1$ is hydrogen or a carboxy protecting group; and $R_2$ hydrogen, acetoxy, methoxy, methylthio, (5-methyl-1,3,4-thiadiazol-2-yl)thio, or (1-methyl-1H-tetrazol-5-yl)thio; which comprises the steps of 1. dehydrating said compound to form the corresponding isoimide having the formula

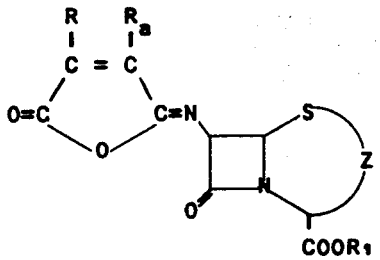

2. reacting said isoimide with a hydrazine of the formula $R_3HNNHR_4$ in which $R_3$ and $R_4$ independently are hydrogen or methyl; and 3. a) reacting the reaction mixture from the aforementioned hydrazine treatment with an acyl halide to produce the corresponding 7-acylamido cephalosporin or 6-acylamido penicillin; or
   b. when at least one of $R_3$ and $R_4$ is methyl, recovering the corresponding 7-amino cephalosporin or 6-amino penicillin from the reaction mixture of the aforementioned hydrazine treatment; or
   c. when $R_3$ and $R_4$ are hydrogen, heating the reaction mixture from the aforementioned hydrazine treatment to a temperature of from about 50°C. to about 100°C. to produce the corresponding 7-amino cephalosporin or 6-amino penicillin; or
   d. when $R_3$ and $R_4$ are hydrogen, reacting the reaction mixture from the aforementioned hydrazine treatment with acid to produce the corresponding 7-amino cephalosporin or 6-amino penicillin in the form of its acid addition salt.

30. Process of claim 29, in which the amic acid compound is dehydrated by treatment with N,N'-dicyclohexylcarbodiimide, an alkyl chloroformate and a tertiary amine, or trifluoroacetic anhydride and a tertiary amine.

31. Process of claim 30, in which the amide acid compound is dehydrated by treatment with N,N'-dicyclohexylcarbodiimide in an inert solvent at a temperature of from about 0°C. to about 30°C.

32. Process of claim 30, in which the amic acid compound is dehydrated by treatment with trifluoroacetic anhydride in the presence of a tertiary amine at a temperature of from about 0°C. to about 30°C.

33. Process of claim 30, in which the amic acid compound is dehydrated by treatment with an alkyl chloroformate in the presence of a tertiary amine at a temperature of from about −20°C. to about +5°C.

34. Process of claim 29, in which the isoimide is first reacted with up to 1 equivalent of a hydrazine in which $R_3$ and $R_4$ are hydrogen per equivalent of the isoimide at a temperature of from about −76°C. to about room temperature for from about 1 to about 10 minutes, and the resulting reaction mixture is reacted with from about 1 to about 2 equivalents of an acid selected from the group consisting of hydrochloric acid, hydrobromic acid, phosphoric acid, p-toluenesulfonic acid, methanesulfonic acid, and sulfuric acid per equivalent of the original isoimide for about 5 to about 10 minutes to produce the corresponding amino cephalosporin or penicillin in the form of its acid addition salt.

35. Process of claim 29, in which the isoimide is first reacted with up to 1 equivalent of a hydrazine in which at least one of $R_3$ and $R_4$ is methyl per equivalent of the isoimide at a temperature of from about −76°C. to about room temperature for from about 1 to about 10 minutes to produce the corresponding amino cephalosporin or penicillin.

36. Process of claim 29, in which $R_1$ is $C_1$–$C_4$ alkyl, 2,2,2-trichloroethyl, benzyl, p-nitrobenzyl, p-methoxybenzyl, benzhydryl, $C_2$–$C_6$ alkanoyloxymethyl, phenacyl, or p-halophenacyl.

37. Process of claim 29, in which R and $R_a$ are hydrogen.

38. Process of claim 29, in which R and $R_a$ taken together with the carbon atoms to which they are attached represent an ortho-phenylene ring.

39. Process of claim 38, in which Z is

40. Process of claim 38, in which Z is

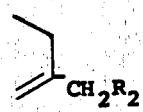

41. Process of claim 40, in which $R_1$ is hydrogen or p-nitrobenzyl.

42. Process of claim 41, in which $R_2$ is hydrogen.

43. Process of claim 41, in which $R_2$ is acetoxy.

44. Process of claim 41, in which $R_2$ is (5-methyl-1,3,4-thiadiazo-2-yl)thio.

45. Process of claim 41, in which $R_2$ is (1-methyl-1H-tetrazol-5-yl)thio.

46. A compound of the formula

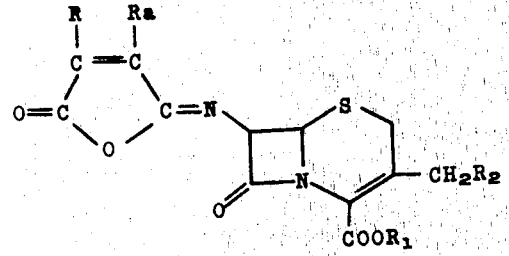

in which R and $R_a$ are hydrogen, or R and $R_a$ taken together with the carbon atoms to which they are attached represent an orthophenylene ring; $R_1$ is hydrogen or a carboxy protecting group; and $R_2$ is hydrogen, acetoxy, methoxy, methylthio, (5-methyl-1,3,4-thiadiazol-2-yl)thio, or (1-methyl-1H-tetrazol-5-yl)thio.

47. Compound of claim 46, in which R and $R_a$ are hydrogen.

48. Compound of claim 46, in which R and $R_a$ taken together with the carbon atoms to which they are attached represent an ortho-phenylene ring.

49. Compound of claim 48, in which $R_1$ is $C_1$–$C_4$ alkyl, 2,2,2-trichloroethyl, benzyl, p-nitrobenzyl, p-methoxybenzyl, benzhydryl, $C_2$–$C_6$ alkanoyloxymethyl, phenacyl, or p-halophenacyl.

50. Compound of claim 48, in which $R_1$ is hydrogen.

51. Compound of claim 49, in which $R_1$ is p-nitrobenzyl.

52. Compound of claim 46, in which $R_1$ and $R_2$ are hydrogen.

53. Compound of claim 46, in which $R_1$ is p-nitrobenzyl and $R_2$ is hydrogen.

54. Compound of claim 46, in which $R_1$ is hydrogen and $R_2$ is acetoxy.

55. Compound of claim 46, in which $R_1$ is p-nitrobenzyl and $R_2$ is acetoxy.

56. Compound of claim 46, in which $R_1$ is hydrogen and $R_2$ is (5-methyl-1,3,4-thiadiazol-2-yl)thio.

57. Compound of claim 46, in which $R_1$ is p-nitrobenzyl and $R_2$ is (5-methyl-1,3,4-thiadiazol-2-yl)thio.

58. Compound of claim 46, in which $R_1$ is hydrogen and $R_2$ is (1-methyl-1H-tetrazol-5-yl)thio.

59. Compound of claim 46, in which $R_1$ is p-nitrobenzyl and $R_2$ is (1-methyl-1H-tetrazol-5-yl)thio.

* * * * *

UNITED STATES PATENT AND TRADEMARK OFFICE
CERTIFICATE OF CORRECTION

PATENT NO. : 4,005,074
DATED : January 25, 1977
INVENTOR(S) : Stjepan P. Kukolja
Steven R. Lammert It is certified that error appears in the above-identified patent and that said Letters Patent are hereby corrected as shown below:

Column 8, line 52, "diketopphthalazine" should read --diketophthalazine--.

Column 12, line 29, "7-phthalisoimido-3-(1,3,4-methyl-1,3,4-thiadiazol-" should read --7-phthalisoimido-3-(5-methyl-1,3,4-thiadiazol- --.

Column 12, line 30, "acid to 77-" should read --acid to 7- --.

Column 17, line 32, "dired" should read --dried--.

Column 17, line 33, "over dried 4" should read --over $MgSO_4$--.

Column 28, line 15, following "lene ring;" and before the drawing, --Z is-- should be inserted.

Column 29, line 25, following "ortho-phenylene ring;" and before the drawing, --Z is-- should be inserted.

Signed and Sealed this

Twenty-eighth Day of June 1977

[SEAL]

Attest:

RUTH C. MASON
Attesting Officer

C. MARSHALL DANN
Commissioner of Patents and Trademarks